US012622717B2

(12) United States Patent
Vo

(10) Patent No.: US 12,622,717 B2
(45) Date of Patent: May 12, 2026

(54) INTRAVASCULAR LITHOTRIPSY CATHETER WITH INTERFERING SHOCK WAVES

(71) Applicant: Shockwave Medical, Inc., Santa Clara, CA (US)

(72) Inventor: Khanh Vo, Daly City, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 81 days.

(21) Appl. No.: 18/660,514

(22) Filed: May 10, 2024

(65) Prior Publication Data

US 2024/0285296 A1      Aug. 29, 2024

Related U.S. Application Data

(60) Continuation of application No. 18/236,631, filed on Aug. 22, 2023, now Pat. No. 12,011,185, which is a
(Continued)

(51) Int. Cl.
*A61B 17/22* (2006.01)
(52) U.S. Cl.
CPC ................... *A61B 17/22022* (2013.01); *A61B 2017/22025* (2013.01); *A61B 2017/22038* (2013.01)
(58) Field of Classification Search
CPC ............ A61B 17/225; A61B 17/22022; A61B 17/22012; A61B 17/22004; A61B 2017/22025
See application file for complete search history.

(56) References Cited

U.S. PATENT DOCUMENTS

| | | |
|---|---|---|
| 2,916,647 A | 12/1959 | George |
| 3,412,288 A | 11/1968 | Ostrander |
| | (Continued) | |

FOREIGN PATENT DOCUMENTS

| | | |
|---|---|---|
| AU | 2009313507 B2 | 11/2014 |
| AU | 2013284490 B2 | 5/2018 |
| | (Continued) | |

OTHER PUBLICATIONS

International Search Report and Written Opinion received for International Patent Application No. PCT/US2022/078216 mailed on Feb. 1, 2023, 6 pages.
(Continued)

*Primary Examiner* — Ashley L Fishback
(74) *Attorney, Agent, or Firm* — Morrison & Foerster LLP

(57) ABSTRACT

The present invention provides a catheter for treating an occlusion in a body lumen. The catheter includes an elongated tube, a first electrode pair and a second electrode pair each configured to generate shock waves. The catheter also includes a flexible polymer enclosure that is fillable with conductive fluid and wrapped circumferentially around at least a portion of the elongated tube such that it surrounds the first and second electrode pairs. The first and second electrode pairs can be arranged relative to one another to promote interference between shock waves generated at the electrode pairs when voltage is delivered across the electrodes of each pair. Electrode pairs can be longitudinally adjacent (spaced a relatively small longitudinal distance apart), longitudinally aligned (at the same longitudinal location), circumferentially offset (offset about the circumference of the catheter), circumferentially aligned (at the same circumferential location), or any combination of any of the above.

40 Claims, 18 Drawing Sheets

Related U.S. Application Data division of application No. 17/967,544, filed on Oct. 17, 2022, now Pat. No. 11,779,363.

(60) Provisional application No. 63/257,397, filed on Oct. 19, 2021.

(56) References Cited

U.S. PATENT DOCUMENTS

| | | |
|---|---|---|
| 3,413,976 A | 12/1968 | Roze |
| 3,524,101 A | 8/1970 | Barbini |
| 3,583,766 A | 6/1971 | Padberg |
| 3,785,382 A | 1/1974 | Schmidt-Kloiber et al. |
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |
| 4,741,405 A | 5/1988 | Moeny et al. |
| 4,809,682 A | 3/1989 | Forssmann et al. |
| 4,813,934 A | 3/1989 | Engelson et al. |
| 4,878,495 A | 11/1989 | Grayzei |
| 4,890,603 A | 1/1990 | Filler |
| 4,900,303 A | 2/1990 | Lemelson |
| 4,990,134 A | 2/1991 | Auth |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,804 A | 4/1992 | Abele et al. |
| 5,116,227 A | 5/1992 | Levy |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,454,809 A | 10/1995 | Janssen |
| 5,472,406 A | 12/1995 | de la Torre et al. |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |
| 5,662,590 A | 9/1997 | de la Torre et al. |
| 5,709,676 A | 1/1998 | Alt |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,090,104 A | 7/2000 | Webster et al. |
| 6,113,560 A | 9/2000 | Simnacher |
| 6,132,444 A | 10/2000 | Shturman et al. |
| 6,146,358 A | 11/2000 | Rowe |
| 6,186,963 B1 | 2/2001 | Schwarze et al. |
| 6,210,408 B1 | 4/2001 | Chandrasekaran et al. |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,939,320 B2 | 9/2005 | Lennox |
| 6,989,009 B2 | 1/2006 | Lafontaine |
| 7,066,904 B2 | 6/2006 | Rosenthal et al. |
| 7,087,061 B2 | 8/2006 | Chernenko et al. |
| 7,241,295 B2 | 7/2007 | Maguire |
| 7,309,324 B2 | 12/2007 | Hayes et al. |
| 7,389,148 B1 | 6/2008 | Morgan |
| 7,505,812 B1 | 3/2009 | Eggers et al. |
| 7,569,032 B2 | 8/2009 | Naimark et al. |
| 7,850,685 B2 | 12/2010 | Kunis et al. |
| 7,853,332 B2 | 12/2010 | Olsen et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Hawkins et al. |
| 9,138,249 B2 | 9/2015 | Adams et al. |
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,433,428 B2 | 9/2016 | Hakala et al. |
| 9,522,012 B2 | 12/2016 | Adams |
| 9,642,673 B2 | 5/2017 | Adams et al. |
| 9,993,292 B2 | 6/2018 | Adams et al. |
| 10,039,561 B2 | 8/2018 | Adams et al. |
| 10,118,015 B2 | 11/2018 | De La Rama et al. |
| 10,149,690 B2 | 12/2018 | Hawkins et al. |
| 10,154,799 B2 | 12/2018 | Van Der Weide et al. |
| 10,159,505 B2 | 12/2018 | Hakala et al. |
| 10,206,698 B2 | 2/2019 | Hakala et al. |
| 10,517,620 B2 | 12/2019 | Adams |
| 10,517,621 B1 | 12/2019 | Adams |
| 10,555,744 B2 | 2/2020 | Nguyen et al. |
| 10,682,178 B2 | 6/2020 | Adams et al. |
| 10,702,293 B2 | 7/2020 | Hawkins et al. |
| 10,709,462 B2 | 7/2020 | Nguyen et al. |

(56) References Cited

U.S. PATENT DOCUMENTS

| | | |
|---|---|---|
| 10,786,267 B2 | 9/2020 | WasDyke et al. |
| 10,888,373 B2 | 1/2021 | Koblish et al. |
| 10,959,743 B2 | 3/2021 | Adams et al. |
| 10,966,737 B2 | 4/2021 | Nguyen |
| 10,973,538 B2 | 4/2021 | Hakala et al. |
| 11,000,299 B2 | 5/2021 | Hawkins et al. |
| 11,020,135 B1 | 6/2021 | Hawkins |
| 11,026,707 B2 | 6/2021 | Ku et al. |
| 11,076,874 B2 | 8/2021 | Hakala et al. |
| 11,337,713 B2 | 5/2022 | Nguyen et al. |
| 11,432,834 B2 | 9/2022 | Adams |
| 11,478,261 B2 | 10/2022 | Nguyen |
| 11,534,187 B2 | 12/2022 | Bonutti |
| 11,596,424 B2 | 3/2023 | Hakala et al. |
| 11,622,780 B2 | 4/2023 | Nguyen et al. |
| 11,696,799 B2 | 7/2023 | Adams et al. |
| 11,771,449 B2 | 10/2023 | Adams et al. |
| 11,779,363 B2 | 10/2023 | Vo |
| 12,011,185 B2 | 6/2024 | Vo |
| 2001/0044596 A1 | 11/2001 | Jaafar |
| 2002/0045890 A1 | 4/2002 | Celliers et al. |
| 2002/0082553 A1 | 6/2002 | Duchamp |
| 2002/0177889 A1 | 11/2002 | Brisken et al. |
| 2003/0004434 A1 | 1/2003 | Greco et al. |
| 2003/0176873 A1 | 9/2003 | Chernenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0074484 A1 | 4/2006 | Huber |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0156129 A1 | 7/2007 | Kovalcheck |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0227992 A1 | 9/2009 | Nir et al. |
| 2009/0230822 A1 | 9/2009 | Kushculey et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0286709 A1 | 11/2010 | Diamant et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall et al. |
| 2012/0157892 A1 | 6/2012 | Reitmajer et al. |
| 2012/0157991 A1 | 6/2012 | Christian |
| 2012/0203255 A1 | 8/2012 | Hawkins et al. |
| 2012/0253358 A1 | 10/2012 | Golan et al. |
| 2013/0030431 A1 | 1/2013 | Adams |
| 2013/0041355 A1 | 2/2013 | Heeren et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0253622 A1 | 9/2013 | Hooven |
| 2014/0005576 A1 | 1/2014 | Adams et al. |
| 2014/0039513 A1 | 2/2014 | Hakala et al. |
| 2014/0046229 A1 | 2/2014 | Hawkins et al. |
| 2014/0214061 A1 | 7/2014 | Adams et al. |
| 2015/0320432 A1 | 11/2015 | Adams |
| 2016/0151081 A1 | 6/2016 | Adams et al. |
| 2016/0324534 A1 | 11/2016 | Hawkins et al. |
| 2017/0135709 A1 | 5/2017 | Nguyen et al. |
| 2017/0311965 A1 | 11/2017 | Adams |
| 2018/0056038 A1 | 3/2018 | Aujla |
| 2018/0256250 A1 | 9/2018 | Adams et al. |
| 2018/0304053 A1 | 10/2018 | Eggert et al. |
| 2019/0150960 A1 | 5/2019 | Nguyen et al. |
| 2019/0388110 A1 | 12/2019 | Nguyen et al. |
| 2020/0085458 A1 | 3/2020 | Nguyen et al. |
| 2020/0297366 A1 | 9/2020 | Nguyen et al. |
| 2020/0397453 A1* | 12/2020 | McGowan ............ A61B 18/26 |
| 2021/0085383 A1 | 3/2021 | Vo et al. |
| 2021/0228137 A1 | 7/2021 | Aujla |
| 2021/0307828 A1 | 10/2021 | Schultheis et al. |
| 2021/0308001 A1 | 10/2021 | Cioanta |
| 2021/0338258 A1 | 11/2021 | Hawkins et al. |
| 2022/0015785 A1 | 1/2022 | Hakala et al. |
| 2022/0240958 A1 | 8/2022 | Nguyen et al. |
| 2022/0280765 A1 | 9/2022 | Tabiliran et al. |
| 2022/0287732 A1 | 9/2022 | Anderson et al. |
| 2023/0043475 A1 | 2/2023 | Adams |
| 2023/0107690 A1 | 4/2023 | Nguyen |
| 2023/0293197 A1 | 9/2023 | Nguyen et al. |
| 2023/0310073 A1 | 10/2023 | Adams et al. |
| 2023/0329731 A1 | 10/2023 | Hakala et al. |
| 2023/0380849 A1 | 11/2023 | Adams et al. |
| 2023/0404605 A1 | 12/2023 | Vo |

FOREIGN PATENT DOCUMENTS

| | | |
|---|---|---|
| CA | 2104414 A1 | 2/1995 |
| CN | 1204242 A | 1/1999 |
| CN | 1269708 A | 10/2000 |
| CN | 1942145 A | 4/2007 |
| CN | 101043914 A | 9/2007 |
| CN | 102057422 A | 5/2011 |
| CN | 102271748 A | 12/2011 |
| CN | 102355856 A | 2/2012 |
| CN | 102765785 A | 11/2012 |
| CN | 203564304 U | 4/2014 |
| CN | 110809448 A | 2/2020 |
| CN | 111388086 B2 | 8/2020 |
| CN | 111601560 A | 8/2020 |
| DE | 3038445 A1 | 5/1982 |
| DE | 202006014285 U1 | 12/2006 |
| EP | 0442199 A2 | 8/1991 |
| EP | 0571306 A1 | 11/1993 |
| EP | 623360 A1 | 11/1994 |
| EP | 0647435 A1 | 4/1995 |
| EP | 2253884 A1 | 11/2010 |

(56) References Cited

FOREIGN PATENT DOCUMENTS

| | | | |
|---|---|---|---|
| EP | 2362798 | B1 | 4/2014 |
| JP | S62-099210 | U | 6/1987 |
| JP | S62-275446 | A | 11/1987 |
| JP | H03-63059 | A | 3/1991 |
| JP | H06-125915 | A | 5/1994 |
| JP | H07-47135 | A | 2/1995 |
| JP | H08-89511 | A | 4/1996 |
| JP | H10-99444 | A | 4/1998 |
| JP | H10-314177 | A | 12/1998 |
| JP | H10-513379 | A | 12/1998 |
| JP | 2002538932 | A | 11/2002 |
| JP | 2004081374 | A | 3/2004 |
| JP | 2004357792 | A | 12/2004 |
| JP | 2005501597 | A | 1/2005 |
| JP | 2005095410 | A | 4/2005 |
| JP | 2005515825 | A | 6/2005 |
| JP | 2006516465 | A | 7/2006 |
| JP | 2007289707 | A | 11/2007 |
| JP | 2007532182 | A | 11/2007 |
| JP | 2008506447 | A | 3/2008 |
| JP | 2011513694 | A | 4/2011 |
| JP | 2011520248 | A | 7/2011 |
| JP | 2011524203 | A | 9/2011 |
| JP | 2011528963 | A | 12/2011 |
| JP | 2012505050 | A | 3/2012 |
| JP | 2012508042 | A | 4/2012 |
| JP | 2015525657 | A | 9/2015 |
| JP | 2015528327 | A | 9/2015 |
| JP | 6029828 | B2 | 11/2016 |
| JP | 6081510 | B2 | 2/2017 |
| JP | 2017176883 | A | 10/2017 |
| JP | 2021503344 | A | 2/2021 |
| WO | WO-1989011307 | A1 | 11/1989 |
| WO | WO-1996024297 | A1 | 8/1996 |
| WO | WO-1999000060 | A1 | 1/1999 |
| WO | WO-1999002096 | A1 | 1/1999 |
| WO | WO-2000056237 | A2 | 9/2000 |
| WO | WO-2004069072 | A2 | 8/2004 |
| WO | WO-2005099594 | A1 | 10/2005 |
| WO | WO-2005102199 | A1 | 11/2005 |
| WO | WO-2006006169 | A2 | 1/2006 |
| WO | WO-2006127158 | A2 | 11/2006 |
| WO | WO-2007088546 | A2 | 8/2007 |
| WO | WO-2007149905 | A2 | 12/2007 |
| WO | WO-2009121017 | A1 | 10/2009 |
| WO | WO-2009126544 | A1 | 10/2009 |
| WO | WO-2009136268 | A2 | 11/2009 |
| WO | WO-2009152352 | A2 | 12/2009 |
| WO | WO-2010014515 | A2 | 2/2010 |
| WO | WO-2010054048 | A2 | 5/2010 |
| WO | WO-2011006017 | A1 | 1/2011 |
| WO | WO-2011094111 | A2 | 8/2011 |
| WO | WO-2011143468 | A2 | 11/2011 |
| WO | WO-2012025833 | A2 | 3/2012 |
| WO | WO-2013059735 | A1 | 4/2013 |
| WO | WO-2014025397 | A1 | 2/2014 |
| WO | WO-2014025620 | A1 | 2/2014 |
| WO | WO-2015017499 | A1 | 2/2015 |
| WO | WO-2018200865 | A1 | 11/2018 |
| WO | WO-2019099218 | A1 | 5/2019 |
| WO | WO-2019174625 | A1 | 9/2019 |

OTHER PUBLICATIONS

Notice of Allowance received for Korean Patent Application No. 10-2024-7016011, mailed on Feb. 6, 2025, 3 pages. English translation.

Notice of Allowance received for Australian Patent Application No. 2024259874, mailed on Feb. 6, 2025, 3 pages.

Office Action received for Brazilian Patent Application No. 11 2024 005807 7, mailed on Oct. 23, 2024, 11 pages. English translation.

Notice of Allowance received for Brazilian Patent Application No. 11 2024 005807 7, mailed on Mar. 11, 2025, 5 pages. English translation.

Office Action received for Chinese Patent Application No. 202280070239.9, mailed on Oct. 18, 2024, 14 pages. English translation.

Notice of Allowance received for Chinese Patent Application No. 202280070239.9, mailed on Mar. 11, 2025, 4 pages. English translation.

Extended European Search Report and Written Opinion received for European Patent Application No. 22884620.0 mailed on Jun. 30, 2025, 8 pages.

Office Action received for Japanese Patent Application No. 2024-523164, mailed on Mar. 14, 2025, 8 pages. English translation.

Office Action received for Mexican Patent Application No. MX/a/2025/000630, mailed on May 26, 2025, 6 pages. English translation.

Notice of Allowance received for Mexican Patent Application No. MX/a/2024/004753, mailed on Nov. 27, 2024, 5 pages. English translation.

Notice of Allowance received for Singaporean Patent Application No. 11202401747Y, mailed on Dec. 16, 2024, 2 pages. English translation.

* cited by examiner

Bubble Formation and Collapse, M5 Catheter (10mm spacing) vs.Lx Catheter (2.5mm,3.5mm,4.5mm spacing)

INTRAVASCULAR LITHOTRIPSY CATHETER WITH INTERFERING SHOCK WAVES

CROSS REFERENCE TO RELATED APPLICATIONS

This is a continuation application of U.S. patent application Ser. No. 18/236,631, filed Aug. 22, 2023, which is a divisional application of U.S. patent application Ser. No. 17/967,544, filed on Oct. 17, 2022, now U.S. Pat. No. 11,779,363, issued Oct. 10, 2023, which claims the benefit of U.S. Provisional Application No. 63/257,397, filed on Oct. 19, 2021, the entire contents of each of which are incorporated herein by reference.

FIELD OF THE DISCLOSURE

The present disclosure relates generally to the field of medical devices and methods, and more specifically to shock wave catheter devices for treating calcified lesions in body lumens, such as calcified lesions and occlusions in vasculature and kidney stones in the urinary system.

BACKGROUND

A wide variety of catheters have been developed for treating calcified lesions, such as calcified lesions in vasculature associated with arterial disease. For example, treatment systems for percutaneous coronary angioplasty or peripheral angioplasty use angioplasty balloons to dilate a calcified lesion and restore normal blood flow in a vessel. In these types of procedures, a catheter carrying a balloon is advanced into the vasculature along a guide wire until the balloon is aligned with calcified plaques. The balloon is then pressurized (normally to greater than 10 atm), causing the balloon to expand in a vessel to push calcified plaques back into the vessel wall and dilate occluded regions of vasculature.

More recently, catheters have been developed that include pairs of electrodes for generating shock waves inside an angioplasty balloon. Shock wave devices can be particularly effective for treating calcified lesions because the acoustic pressure from the shock waves can crack and disrupt lesions near the angioplasty balloon without harming the surrounding tissue. In these devices, the catheter is advanced over a guidewire through a patient's vasculature until it is positioned proximal to and/or aligned with the calcified lesion in a body lumen. The balloon is then inflated with conductive fluid (using a relatively low pressure of 2-4 atm) so that the balloon expands to contact the lesion. Voltage can then be applied to the electrodes of the electrode pairs to produce acoustic shock waves that propagate through the walls of the angioplasty balloon and into the lesions. Once the lesions have been cracked by the acoustic shock waves, the balloon can be expanded further to increase the cross-sectional area of the lumen and improve blood flow through the vessel.

Efforts have been made to improve the delivery of shock waves in these devices, for instance, by directing shock waves in a forward direction to break up tighter and harder-to-cross occlusions in vasculature. Examples of forward-firing designs can be found in U.S. Pat. No. 10,966,737 and U.S. Publication Nos. 2019/0388110, both of which are incorporated herein by reference. Other catheter devices have been designed to include arrays of low-profile electrode assemblies that reduce the crossing profile of the catheter and allow the catheter to more easily navigate calcified vessels to deliver shock waves in more severely occluded regions of vasculature. For instance, U.S. Pat. Nos. 8,888,788, and 10,709,462, both of which are incorporated herein by reference, provide examples of low-profile electrode assemblies.

Despite these advances, many currently available shock wave catheters have challenges producing shock waves with sufficient acoustic pressure to treat dense and hard-to-crack calcium, or eccentric calcium, in large arterial vessels. First, the total lesion-cracking energy delivered by shock wave catheters is limited by the voltage source used to induce shock wave formation. While many conventional shock wave catheter devices use high voltage pulse generators, these generators deliver only a limited range of voltages, and extremely high voltages can risk rupturing the catheter balloon and damaging a patient's vasculature during shock wave treatments. Second, many shock wave catheter designs distribute energy to an electrode assembly with more than one pair of electrodes connected in series and spaced out along the catheter at a distance of six millimeters (6 mm) or more apart. When spacing electrode pairs more than 6 mm apart from one another, the acoustic shock waves generated by each of the electrode pairs may propagate individually with minimal overlap to adjacent waves, resulting in the delivery of lower pressure single-wavefront shock waves. Additionally, when connecting multiple electrode pairs in series on the same voltage channel, the voltage is evenly distributed among the electrodes, which reduces the peak pressure of shock waves generated at each electrode pair thereby producing an array of shock waves having a relatively lower peak pressure. Third, some current shock wave catheter designs include emitters that each include a pair of electrode pairs that are arranged circumferentially 180 degrees apart from each other. When circumferentially separated by 180 degrees on an emitter, the acoustic shock waves emitted from those electrode pairs propagate individually in opposite directions, with minimal overlap to the shock waves of the corresponding electrode pair at the same longitudinal location (i.e., on the same emitter). Accordingly, there is an unmet need for catheter designs capable of producing increased pressure acoustic shock waves using conventional voltage generators. Similar devices are needed for treating occlusions formed in other parts of the body, for example, kidney stones in the urinary system.

BRIEF SUMMARY

The above objects are realized in a catheter that includes an electrode assembly with electrode pairs located proximate to one another such that the shock waves emitted from each electrode pair constructively interfere with one another. When shock waves generated from electrode pairs that are proximate to one another constructively interfere, the combined shockwave has a higher pressure than the shock waves of each individual emitter, which enables the combined shock wave to treat denser and more rigid calcified lesions in a body lumen.

In one or more examples, electrode pairs located inside a flexible enclosure of a catheter are spaced a relatively small distance apart from one another (e.g., 1 mm-4 mm apart) along the length of the catheter. Spacing the electrode pairs a relatively small distance from one another promotes constructive interference between acoustic shock waves generated at the adjacent electrode pairs, thereby increasing the pressure of the combined shock wave. In one or more examples, the catheter can include one or more emitters that each includes a pair of electrode pairs that are located at the same longitudinal location along the length of the catheter (i.e., on the same emitter) with the electrode pairs arranged circumferentially less than 180 degrees apart from each other on the emitter. Arranging electrode pairs of the same emitter at an angle less than 180 degrees apart promotes constructive interference between acoustic shock waves generated at the adjacent electrode pairs, thereby increasing the pressure of the combined shock wave. When the catheter includes multiple emitters (each including pairs of electrode pairs that are separated by less than 180 degrees relative to one another on the emitter), the emitters can be spaced a relatively small distance apart from one another (e.g., 1 mm-4 mm apart) along the length of the catheter. Spacing the emitters a relatively small distance from one another promotes constructive interference between acoustic shock waves generated at the adjacent emitters, thereby increasing the pressure of the combined shock wave.

An exemplary implementation provides a catheter for treating an occlusion in a body lumen. The catheter includes an elongated tube and a flexible polymer enclosure that is fillable with a conductive fluid and wrapped circumferentially around at least a portion of the elongated tube. The catheter also includes a first electrode pair and second electrode pair located inside the flexible enclosure that each include a first electrode and second electrode configured to generate shock waves when voltage is delivered to the electrodes. The electrodes of each electrode pair are separated by a distance that is generally referred to as a spark gap where electricity will cross (jump) through conductive fluid and generate a vapor bubble.

In one or more examples, the gaps between the electrodes of each electrode pair can be circumferentially aligned with one another relative to the elongated tube (e.g., the gap between the first electrode and second electrode of the first electrode pair can be located at the same location along the circumference of the catheter as the gap between the first electrode and second electrode of the second electrode pair) and separated by a distance (e.g., a longitudinal gap) between 1 mm and 4 mm along the length of the catheter such that the shock waves generated at the electrode pairs constructively interfere to produce a combined shock wave.

In another implementation, the gaps between the electrodes of each electrode pair can be circumferentially offset from one another relative to the elongated tube by an angle of less than 180 degrees but located at essentially the same longitudinal location on the elongated tube such that the shock waves generated at the electrode pairs constructively interfere to produce a combined shock wave. When located at the same longitudinal location, electrode pairs can be termed to be located on the same "emitter." Thus, a catheter including an emitter includes one or more electrode pairs at the same longitudinal location.

Optionally, the catheter can include multiple adjacent emitters configured to generate shock waves that constructively interfere with one another. When voltage is delivered to the emitters, the individual shock waves generated at the electrode pairs of adjacent emitters can constructively interfere with one another to form a combined shock wave, provided that the circumferential and/or longitudinal gaps between the electrode pairs allow the electrode pairs on adjacent emitters to remain sufficiently proximate relative to one another.

In one or more examples, the catheter can include a first emitter, with a first and second electrode pair circumferentially offset from one another by an angle of 180 degrees, and a second emitter, with a third and fourth electrode pair circumferentially offset from one another by an angle of 180 degrees, where the first emitter and second emitter are separated by a longitudinal gap between 1 mm and 4 mm and arranged such that at least one electrode pair of the first emitter is circumferentially aligned (e.g., located at the same circumferential location of the catheter but spaced apart longitudinally) with an electrode pair of the second emitter.

Similarly, in another example, the first emitter and the second emitter can each include a first and second electrode pair circumferentially offset from one another by an angle of less than 180 degrees, with the first and second emitter separated by a longitudinal gap between 1 mm and 4 mm and arranged such that at least one electrode pair of the first emitter is circumferentially aligned with an electrode pair of the second emitter. Optionally, none of the electrode pairs of the first emitter and second emitter are circumferentially aligned with one another.

DESCRIPTION OF THE FIGURES

Illustrative aspects of the present disclosure are described in detail below with reference to the following drawing figures. It is intended that the embodiments and figures disclosed herein are to be considered illustrative rather than restrictive.

DETAILED DESCRIPTION

Figure 1:
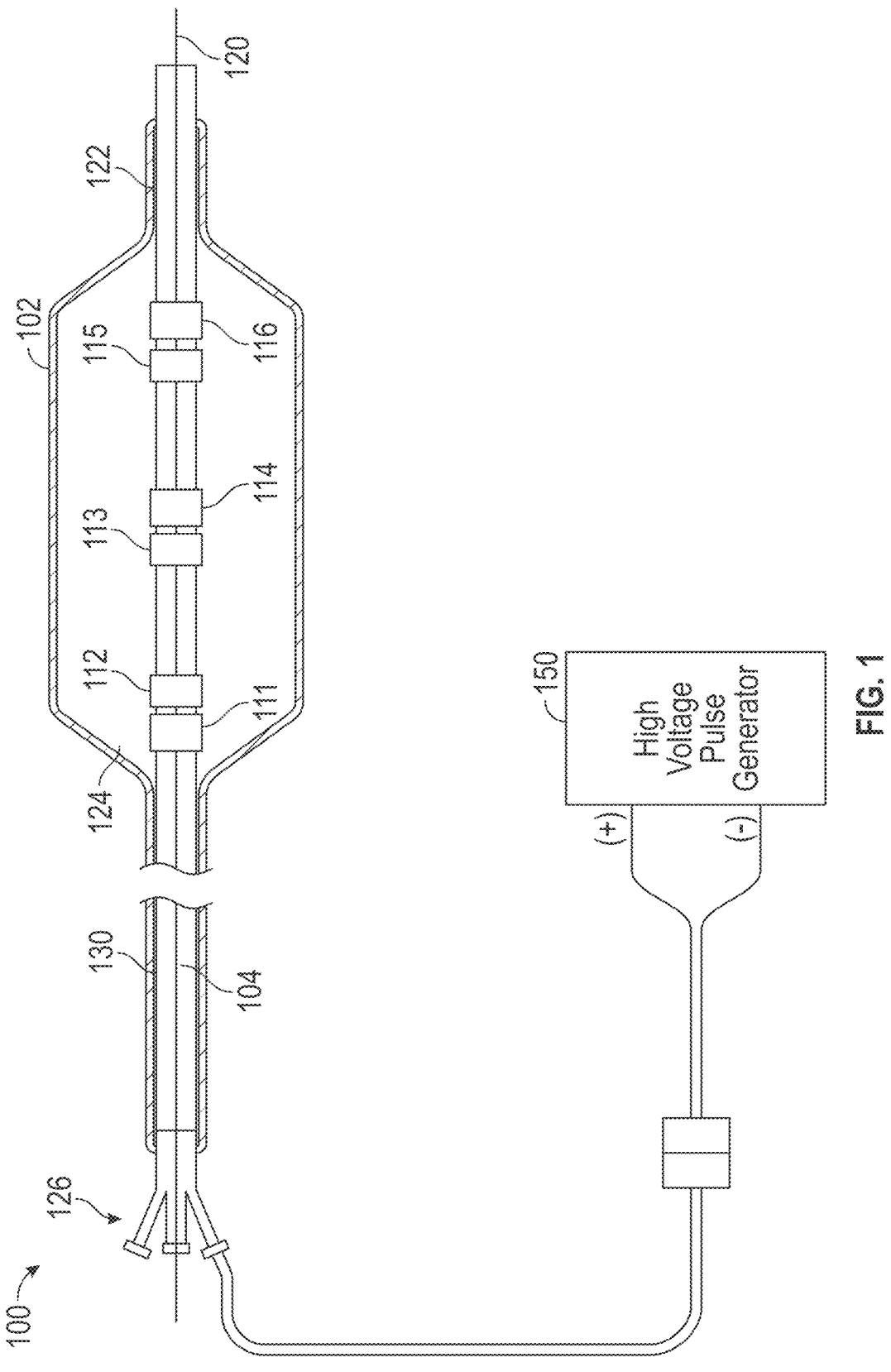
FIG. 1 illustrates an exemplary catheter having an array of emitters inside an angioplasty balloon, according to aspects of the present disclosure.

The following description is presented to enable a person of ordinary skill in the art to make and use the various embodiments and aspects thereof disclosed herein. Descriptions of specific devices, assemblies, techniques, and applications are provided only as examples. Various modifications to the examples described herein will be readily apparent to those of ordinary skill in the art, and the general principles described herein may be applied to other examples and applications without departing from the spirit and scope of the various embodiments and aspects thereof. Thus, the various embodiments and aspects thereof are not intended to be limited to the examples described herein and shown, but are to be accorded the scope consistent with the claims.

As used herein, the term "electrode" refers to an electrically-conducting element (typically made of metal) that receives electrical current and subsequently releases the electrical current to another electrically-conducting element. In the context of the present disclosure, electrodes are often positioned relative to each other as an inner electrode and an outer electrode. Accordingly, as used herein, an "electrode pair" refers to two electrodes that are positioned adjacent to each other such that an electrical current will transmit across the gap between the two electrodes (e.g., between an inner electrode and an outer electrode, or vice versa, optionally with an insulation separating the two electrodes, and with the electricity passing through a conductive fluid or gas therebetween). In some contexts, one or more electrode pairs (positioned across one or more emitters) may also be referred to as an electrode assembly. Further, as used herein, an "emitter" refers to a structure that has one or more electrode pairs. Emitters can be singular, paired, or otherwise arranged together to be electrically connected as an emitter assembly. Shock waves can be generated at each electrode pair of an emitter.

Described herein are catheters incorporating design elements that improve the efficiency and increase the peak pressure of acoustic shock waves delivered from a shock wave catheter device. In one or more examples, the catheters include electrode assemblies of emitter pairs having reduced spacing between adjacent emitters to promote interference between shock waves generated at the electrode pairs of the adjacent emitters. When electrode pairs of adjacent emitters are activated together, the acoustic pressure wavefronts of the shock waves can constructively interfere to produce an overlapping or combined acoustic pressure wavefront (i.e., a combined shock wave). In one or more examples, the catheters described herein include emitter assemblies with electrode pairs located on separate adjacent emitters that are proximate to one another longitudinally on the catheter, such as spaced apart by a longitudinal gap between one to four millimeters (1 mm to 4 mm).

In one or more examples, the catheters described herein include emitter assemblies having a pair of electrodes located at the same longitudinal location on the catheter (and on the emitter). The electrode pairs of an emitter can be circumferentially offset (e.g., spaced apart) from one another by 180 degrees, or by less than 180 degrees. Optionally, a first electrode pair on a first emitter at a first longitudinal location can be located proximate to a second electrode pair on a second emitter and spaced apart longitudinally on the catheter. The electrode pairs on each of the first emitter and the second emitter can be arranged such that that they are circumferentially aligned with one another (e.g., the first electrode pair of the first emitter positioned at the same circumferential location as the first electrode pair of the second emitter) or such that they are offset from one another (e.g., the first electrode pair of the first emitter circumferentially offset from the first electrode pair of the second emitter). In one or more examples, the catheters described herein include electrode assemblies having an emitter with a single electrode pair and/or a single emitter with a pair of electrode pairs.

As used herein, a "combined shock wave" includes two or more shock waves produced by closely-spaced adjacent emitter pairs that are activated together (for instance, activated by the same high voltage pulse, which causes shock waves to be generated simultaneously or only a few nanoseconds apart). Constructive interference between adjacent shock waves can result in high amplitude combined shock waves having a higher peak pressure compared to shock waves delivered from a conventional shock wave catheter with relatively increased emitter spacing (see, e.g., the peaks of the graphs in FIG. 7). Closely spaced electrode pairs and/or closely spaced emitters can also produce combined shock waves having overlapping higher pressure multiple (e.g., double) wavefronts that propagate at slightly different angles, producing a "double pounding" effect that delivers increased mechanical force and shear stress to a lesion (see, e.g., the bottom row pressure wavefronts shown in FIG. 6).

The catheter designs described herein may be similar to current shock wave catheters in that they include an array of miniaturized emitters each having one or more electrode pairs along a catheter (e.g., within the working length of an angioplasty balloon) that deliver acoustic shock waves to a treatment site surrounding the catheter. However, in one example, the present design arranges adjacent emitters approximately 3.5 mm or less apart along the length of the catheter. In some examples, adjacent emitters are arranged in pairs, with each pair of adjacent emitters spaced apart by 3.5 mm or less. In some implementations, the longitudinal distance between two adjacent emitters is more precisely the distance between the midpoints of two sets of electrode pairs, one on each emitter, where the electrode pairs can be on the edge of the emitter and/or more centrally located within the body of the emitter. When the longitudinally-varied but closely-spaced emitters are fired together, the bubbles generated from the adjacent emitters grow and collapse toward each other to produce combined shock waves. In one or more examples, the pair of electrode pairs on each emitter are located at the same longitudinal location on the catheter but circumferentially spaced apart from one another by less than 180 degrees, such as for example by 120 degrees, 90 degrees, or 60 degrees, and increments and gradients of range therein. Exemplary ranges for the circumferential offset can include, but are not limited to, angles within the ranges of between 40 degrees and 140 degree, 65 degrees and 125 degrees, 80 degrees and 100 degrees, and the like. Accordingly, arrangements of electrodes and emitters as disclosed herein provide for implementations of shock wave generation that impart directionality or a directional bias to the progression of a shock wave. When the longitudinally aligned but circumferentially-varied emitters are fired together, the bubbles generated from the adjacent emitters grow and collapse toward each other to produce combined shock waves. The increased peak pressure and double wavefronts of the combined shock waves maximize the calcium cracking effectiveness of the catheter, which may be particularly beneficial for treating dense and hard-to-crack calcium, eccentric calcium, as well as calcium in large arterial vessels. Moreover, a shock wave having an increased strength can maintain a therapeutic level of force in balloons of a relatively large diameter where there is a greater distance for the shock waves to travel from the emitters to the target tissue region.

FIG. 1 illustrates an exemplary catheter 100 having an array of emitters inside an angioplasty balloon, according to aspects of the present disclosure. The catheter 100 includes a shaft, more specifically an elongated tube 104, extending between a proximal handle 126 of the catheter and a distal tip of the catheter. A flexible polymer enclosure 102 (e.g., a flexible angioplasty balloon or some other compliant or semi-compliant polymeric enclosure) is wrapped circumferentially around at least a portion of the elongated tube 104 and is sealed to the elongated tube 104 via a seal 122 located near the distal tip of the catheter 100. The flexible polymer enclosure 102 forms an annular cavity 124 around the elongated tube 104 that can be filled with a conductive fluid, such as saline or saline mixed with a contrast agent, to fill and/or inflate the flexible polymeric enclosure 102. The conductive fluid may be admitted into the cavity 124 via fill ports located in the proximal end handle 126. The flexible polymeric enclosure 102 also surrounds a number of emitters 111, 112, 113, 114, 115, 116 that are located inside the flexible polymeric enclosure 102 that are configured to generate shock waves in the conductive fluid inside the cavity 124. As shown, the emitters can be arranged in pairs, with emitters 111 and 112 as a proximal pair, emitters 113 and 114 as a central pair, and emitters 115 and 116 as a proximal pair. Collectively, emitters 111, 112, 113, 114, 115, 116 can be referred to as an emitter assembly.

The elongated tube 104 may include a number of lumens (e.g., longitudinal channels through the tube 104) extending between the proximal handle 126 and the distal end of the catheter 100. For instance, the elongated tube 104 may include a fluid lumen for carrying conductive fluid between a fluid port and the cavity 124 of the flexible polymer enclosure 102 in order to fill (i.e., inflate) and/or evacuate the enclosure 102 during a shock wave treatment. The elongated tube 104 may also include a guide wire lumen sized to receive a guide wire 120 to facilitate the insertion and positioning of the catheter 100. In such examples, the catheter 100 may be configured to be advanced into the body lumen over the guide wire 120, generally referred to as an "over-the-wire" or "OTW" arrangement. (In alternative implementations, the catheter may be arranged as part of a "rapid exchange" or "Rx" configuration where instruments are swapped in and out of a lumen in a patient during a procedure.) The elongated tube 104 may also include a number of wire lumens for retaining wires (e.g., polyimide-insulated copper wires) that carry a current between a high voltage pulse generator 150 and the emitters 111, 112, 113, 114, 115, 116. Additionally or alternatively, the outer surface of the elongated tube 104 may include a number of longitudinal grooves or channels configured for retaining wires, and the insulated wires may extend along the grooves in the outer surface of the elongated tube 104.

Shock waves can be generated inside the flexible polymer enclosure 102 at a number of emitters 111, 112, 113, 114, 115, 116 spaced along the length of the elongated tube 104. In some examples, the emitters 111, 112, 113, 114, 115, 116 are formed from conductive metal sheaths and insulated wires positioned around or mounted onto an outer surface of the elongated tube 104. High voltage pulses are supplied to the emitters 111, 112, 113, 114, 115, 116 from a high voltage pulse generator 150 external to the catheter 100. In some examples, the high voltage pulse generator 150 includes a multiplexer for selectively applying a voltage across a particular emitter (e.g., emitter 111) or a pair of emitters (e.g., emitters 111 and 112), to generate shock waves at a desired position within the flexible polymer enclosure 102. Accordingly, emitters or emitter pairs as shown can be connected on the same or separate electrical channels, with the flow of current to a given channel controlled via the multiplexer. In other examples, high-energy lasers are used to generate shock waves by pulsing laser light inside the flexible polymer enclosure 102. In such an example, the catheter 100 could include two or more optical fibers, wherein the output ends thereof are closely spaced together to generate constructively interfering shock waves.

In operation, a physician inserts a guide wire 120 through the guide wire lumen and into a body lumen, and then advances the catheter 100 into the body lumen over the guide wire 120, using the guide wire 120 to maneuver the elongated tube 104 into position at or proximate to a target lesion. Once positioned at a lesion, the cavity 124 can be filled with conductive fluid to at least partially inflate the flexible polymer enclosure 102 (e.g., to a pressure of approximately 4 atm). When inflated, the flexible polymer enclosure 102 gently contacts and/or conforms to the walls of the lumen in direct proximity with a calcified lesion and provides a space between the emitters 111, 112, 113, 114, 115, 116 and the walls of the flexible polymer enclosure 102. The variable high voltage pulse generator 150 can then be activated to deliver a series of high voltage pulses across one or more of the emitters 111, 112, 113, 114, 115, 116 to generate shock waves within the flexible polymer enclosure 102.

Each voltage pulse applied by the generator 150 creates a potential difference across each electrode pair on the emitters. The duration and magnitude of the voltage pulse is sufficient to generate a gas bubble within the conductive fluid on the surface of an electrode. Eventually, a plasma arc of electric current is formed that traverses the bubble and creates a rapidly expanding and collapsing bubble that creates an acoustic shock wave in the flexible polymer enclosure 102. The magnitude and other characteristics of a shock wave can be controlled by adjusting the shock gap distance between the electrodes of an electrode pair, the surface area of the electrodes, the shape of the electrodes, and/or the distance (with respect to the longitude and/or circumference of the catheter) between adjacent electrode pairs. For instance, when adjacent electrode pairs on separate emitters are spaced closely together (longitudinally and/or circumferentially) and activated at the same time, the bubbles formed at these adjacent electrode pairs can expand and collapse together to create combined acoustic shock waves.

The combined acoustic shock waves are conducted through the conductive fluid in the cavity 124, through the walls of the flexible polymer enclosure 102, and into a blood vessel wall where the acoustic shock wave energy can break up calcified lesions and hardened plaque. The size of the bubbles and the rate of expansion and collapse of the bubbles (and therefore the duration and the magnitude of the resulting combined acoustic shock waves) can be controlled by adjusting the magnitude, duration, and repetition rate of the voltage pulses applied by the high voltage pulse generator 150. In some examples, a physician may start a procedure with low energy shock waves and increase the energy as needed to crack the calcified plaques.

As depicted in FIG. 1, the emitters 111, 112, 113, 114, 115, 116 may be arranged in various groupings or pairs spaced along the length of the elongated tube 104, such that combined shock waves can be generated to treat lesions proximate to various portions of the flexible polymeric enclosure 102. The location of the shock waves can be controlled by selectively applying a voltage across a desired emitter and/or a desired grouping or pair of emitters. For instance, the catheter 100 shown in FIG. 1 includes a proximal pair including a first emitter111 and a second emitter 112 located inside a proximal portion of the flexible polymer enclosure 102, a central pair including a third emitter 113 and a fourth emitter 114 located inside a central portion of the flexible polymer enclosure 102, and a distal pair including a fifth emitter 115 and a sixth emitter 116 located inside a distal portion of the flexible polymer enclosure 102. The spacing between adjacent emitters of each pair (e.g., a distance between the first emitter 111 and the second emitter 112 of the proximal pair) is selected to promote constructive interference between shock waves produced by each pair of emitters. In some examples, the emitters of separate groupings or pairs may be spaced apart by a distance sufficient to avoid constructive interference between certain emitters (e.g., to avoid interference between the shock wave generated by the second emitter 112 of the proximal pair and the shock wave generated by the third emitter 113 of the central pair). Moreover, the distance of separation between all emitters can be selected to avoid destructive interference between generated shock waves.

To ensure adjacent emitters fire at approximately the same time (e.g., simultaneously or within nanoseconds), exemplary catheter designs can include electrode assemblies having two or more emitters connected in series on a single independent wiring channel. For instance, each of the proximal, central, and distal pairs of emitters may be wired as an independent electrode assembly that can be activated separately (e.g., the electrodes of emitters in a given electrode assembly can be electrically connected in series such that a single high voltage pulse activates all emitters of the electrode assembly). For instance, the proximal pair including the first emitter 111 and the second emitter 112 could be wired together in a first electrode assembly. The central and distal emitter pairs may be wired in respective further electrode assemblies, such that the emitters of the central and distal pair may be activated independently from the proximal pair and from each other. A single high voltage pulse can be applied across a desired electrode assembly to activate, e.g., emitters 111 and 112 together, or, alternatively, emitters 113 and 114 together, or, alternatively, emitters 115 and 116 together, at approximately the same time. In a further embodiment, a high voltage pulse can be directed to and across an electrode assembly including emitters 111, 112, and 113 together, and then additionally or alternatively to an electrode assembly including emitters 114, 115, and 116 together, at approximately the same time. In other examples, all of the emitters 111, 112, 113, 114, 115, 116 of the catheter 100 are wired in series, such that the application of a single high voltage pulse activates of all of the emitters at approximately the same time (or in other words, in a rapid sequential progression, effectively concurrent for therapeutic function). The constructive interference between closely-spaced adjacent emitters may reduce or mitigate any pressure decreases resulting from the distribution of a high voltage pulse across multiple emitters wired in series.

Figure 2A:
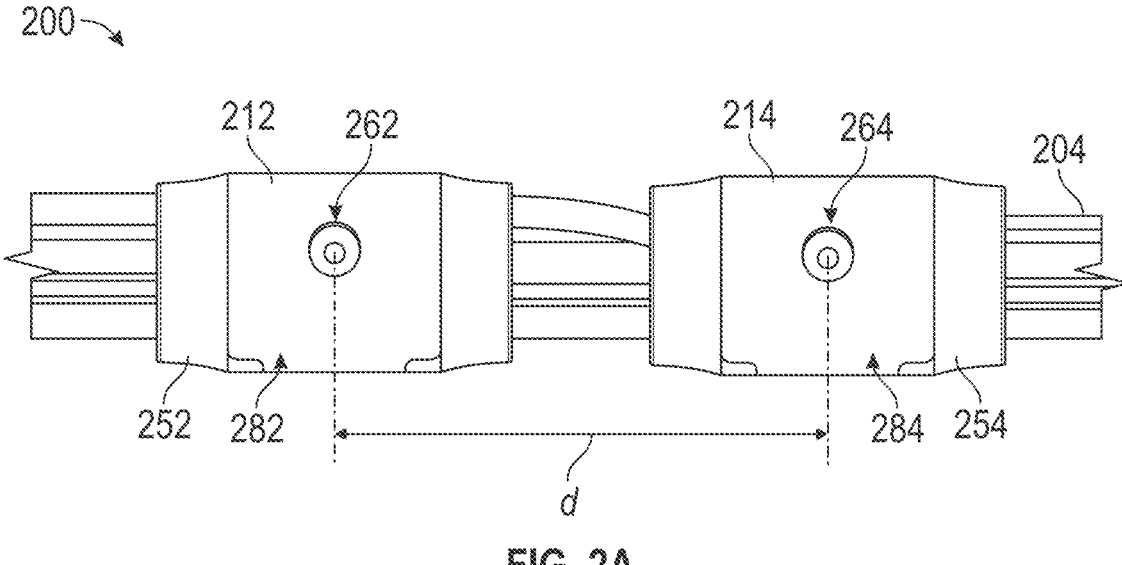
FIG. 2A illustrates the spacing of adjacent emitters with exemplary electrode assemblies formed from insulated wires and conductive sheaths having circular cut-outs, according to aspects of the present disclosure.
Figure 2B:
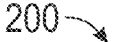
FIG. 2B illustrates the spacing of adjacent emitters with exemplary electrode assemblies formed from insulated wires and conductive sheaths having arcuate cut-outs, according to aspects of the present disclosure.
Figure 2B:
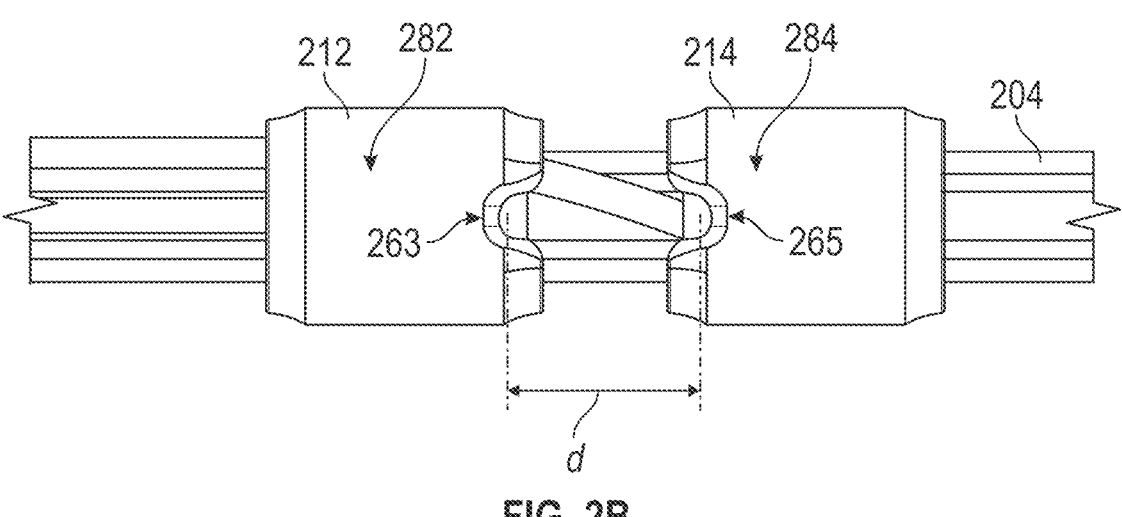

FIGS. 2A-B illustrate two exemplary electrode assemblies 200 that can be included in a catheter, such as an electrode assembly corresponding to the proximal pair, the central pair, or the distal pair of emitters shown in FIG. 1. Each emitter of an electrode assembly (e.g., any of the assemblies shown in FIG. 1, FIGS. 2A-B, FIGS. 3A-B, FIGS. 4A-D, FIG. 9, FIGS. 13A-B, and FIGS. 17-18, and described throughout the disclosure) includes an inner electrode and an outer electrode that form an electrode pair, spaced apart by a spark gap across which current flows to generate shock waves and/or cavitation bubbles. For instance, as described in U.S. Pat. No. 10,709,462, each emitter (e.g., each pair of electrodes) of a catheter may be formed from an edge of the conductive metal sheath and a conductive portion of an insulated wire extending along the catheter. In a particular example, an outer electrode of each electrode pair is formed from a conductive sheath, and an inner electrode is formed by removing a portion of an insulated wire (e.g., cutting a hole in the insulating layer near the end of the wire) to expose an electrically conductive portion of the insulated wire (i.e., an insulation removed portion). In one or more examples, the inner electrodes may be formed from conductive sheaths and the outer electrodes may be formed from electrically conductive portions of insulated wires. The electrically conductive portions of the wires are separated from the conductive sheath by a controlled distance (i.e., a spark gap) to allow for a reproducible arc of energy across the electrodes for a given current and voltage. In some examples, two or more electrode pairs may be formed on the same emitter using a single conductive sheath by positioning two or more electrically conductive portions of insulated wires proximate to the sheath to create two spark gaps across which current can flow to generate a shock wave.

Returning to FIG. 2A, the exemplary electrode assembly 200 includes at least a first electrode pair 262 and a second electrode pair 264 formed from a first conductive sheath 212 and a second conductive sheath 214, respectively, mounted circumferentially around an elongated tube 204 and a series of insulated wires extending along the outer surface of the elongated tube 204. As shown, first electrode pair 262 resides on first emitter 282 and second electrode pair 264 resides on second emitter 284. Referring to FIG. 2B, the exemplary electrode assembly 200 includes at least a first electrode pair 263 and a second electrode pair 265 formed from a respective first conductive sheath 212 and a second conductive sheath 214, respectively, mounted circumferentially around an elongated tube 204 and a series of insulated wires extending along the outer surface of the elongated tube 204. As shown, first electrode pair 263 resides on first emitter 282 and second electrode pair 265 resides on second emitter 284. In some examples, and as will be described further below, each electrode assembly further includes a third electrode pair and a fourth electrode pair (not shown) formed from the respective first conductive sheath 212 and the second conductive sheath 214, respectively (in other words, electrode pairs that share the same or nearly the same longitudinal location as electrode pairs 262 and 264 (or electrode pairs 263 and 265) but are circumferentially offset from one another on each emitter 282 and 284).

In the exemplary electrode assembly 200 shown in FIG. 2A, each conductive sheath 212, 214 includes a circular cut-out, and current is configured to flow between the circular cut-out and an electrically conductive portion of an insulated wire (i.e., an insulation removed portion of the wire) to generate shock waves. In FIG. 2B, the side edge of each conductive sheath 212, 214 of the assembly includes an arcuate cut-out, and current is configured to flow between the arcuate cut-out and an electrically conductive portion of an insulated wire to generate shock waves. In some examples, an insulation sheath 252, 254 is positioned between the electrically conductive portions of the wires and each conductive sheath to prevent unintended current flow between the conductive portions of the wires and the con- ductive sheaths 212, 214. The insulation sheath 252, 254 may include one or more holes or cut-outs positioned at the gaps between each of the conductive portions of the wires and the conductive sheaths 212, 214, providing a path through which current can flow between electrodes of each emitter.

Optionally, an electrode pair can be formed from an electrode assembly without a sheath. For instance, a pair of wires can be located proximate one another, each containing an electrically conductive portions (such as an insulation removed portion), with current configured to flow between the electrically conductive portions of the wires. In such examples, the current can jump from a conductive portion of a first wire to a conductive portion of a second wire thereby generating a shock wave.

Each electrode pair of the assembly 200 has a longitudinal location along the length of the elongated tube 204 and has a circumferential location around the circumference of the elongated tube 204. The longitudinal distance and/or cir- cumferential offset between adjacent emitters and/or adja- cent electrode pairs can be controlled to promote construc- tive interference between shock waves generated at the first emitter 282 and the second emitter 284. As shown in FIGS.

2A, the first emitter 282 and the second emitter 284, and their respective electrode pairs 262, 264, are circumferen- tially aligned (i.e., located at the same circumferential loca- tion) and longitudinally separated by a distance "d". Simi- larly in FIG. 2B, the first emitter 282 and the second emitter 284, and their respective electrode pairs 263, 265, are circumferentially aligned and longitudinally separated by a distance "d", where this distance is different between the two configurations of the emitter assembly.

When emitters of an electrode assembly are arranged in sufficiently close groupings or pairs based on close longi- tudinal proximity to one another (e.g., arranged together in a proximal pair, a central pair, or a distal pair along the length of the catheter as shown in FIGS. 1 and 4A-D), the term longitudinally-adjacent indicates that the elements are arranged together in the same grouping or pair along the length of the catheter. For instance, the first emitter 282 and the second emitter 284 in FIGS. 2A and 2B may properly be considered longitudinally-adjacent emitters, while the sec- ond emitter 112 and the third emitter 113 in FIG. 1 may not be considered longitudinally-adjacent because they corre- spond to separate emitter pairs. Accordingly, a catheter described as having 3.5 mm spacing between longitudinally- adjacent emitters may include a series of emitters arranged in pairs, with the respective electrode pairs of the emitters spaced 3.5 mm from one another. In such an embodiment, the distance between the pairs of longitudinally-adjacent emitters may be 3.5 mm, while emitters of separate pairs may be spaced by greater than 3.5 mm from one another (see, e.g., FIG. 1 where the proximal emitter pair shows the longitudinally-adjacent emitters located closely proximate to one another but separated from the central emitter pair by a distance that is greater than the separation between emit- ters 111 and 112). In one or more examples, the distance between a first electrode pair of a first emitter and a first electrode pair of a second emitter can be greater than a distance between a second electrode pair of the first emitter and a second electrode pair of the second emitter. In other embodiments, dependent on the construction and power supplied to the emitter assembly, the distance between emitters and their respective electrode pairs that qualifies as longitudinally-adjacent may range from 1 mm to 4 mm, or increments and gradients of length in that range.

As used herein, the longitudinal distance ("d") between two adjacent emitters defines the distance between electrode pairs formed from two adjacent conductive sheaths (e.g., in FIG. 2A, the distance between the first electrode pair 262 and the second electrode pair 264 formed from the respec- tive first conductive sheath 212 and second conductive sheath 214), rather than the distance between two electrode pairs formed from a single conductive sheath (e.g., a cir- cumferential distance or offset between the first electrode pair 262 and a third emitter (not shown) formed from the same conductive sheath 212). As used herein, the circum- ferential offset (angle "a") between two emitters formed from a single conductive sheath (i.e., on the same emitter) defines the angle that those electrode pairs are offset from one another (e.g., an offset of 180 degrees indicates the electrode pairs are located on opposite sides of the sheath). When longitudinally-adjacent electrode pairs are located at the same circumferential location of the catheter (e.g., an offset of zero degrees), those electrode pairs can be said to be circumferentially aligned.

The longitudinal distance and/or circumferential offset between adjacent electrode pairs can be measured with respect to the gaps between respective electrode pairs. For instance in FIG. 2A, given an example distance of 3.5 mm between the first emitter 282 and the second emitter 284 indicates that the spark gap between electrodes of the first electrode pair 262 is approximately 3.5 mm from the spark gap between electrodes of the second electrode pair 264. In one or more examples, the longitudinal distance between adjacent electrode pairs may alternatively be approximated by a distance between adjacent conductive sheaths. For instance in FIG. 2B, given an example distance of less than 3.5 mm indicates that the longitudinal distance between a side edge of a first conductive sheath 212 that forms an arcuate electrode pair 263 of the first emitter 282 and a side edge of a second conductive sheath 214 that forms an electrode of the arcuate electrode pair 265 of the second emitter 284. Additionally or alternatively, the distance and/or circumferential offset between adjacent emitters may be approximated by the spacing or circumferential offset of the insulation removed portions of insulated wires that form electrode pairs of the emitters.

As described previously, longitudinally-adjacent emitters of a pair may be spaced a relatively short longitudinal distance apart (e.g., 4 mm or less) to promote constructive interference between shock waves generated at the electrode pairs of the respective emitters. In some examples, the distance between a gap of the electrode pair 262 of a first emitter 282 and a gap of the electrode pair 264 of the second emitter 284 is between 1 mm and 4 mm such that when a voltage is delivered across the first electrode pair 262 and the second electrode pair 264, shock waves generated at the first emitter 282 and the second emitter 284 interfere to produce a combined shock wave.

The circumferential offset between electrode pairs on adjacent emitters can also impact constructive interference among emitters. For instance, the longitudinal distance and the circumferential offset between the first electrode pair 262, 263 and the second electrode pair 264, 265 can be selected such that a combined shock wave forms when the first emitter 282 and the second emitter 284 are activated together (i.e., activated by the same high voltage pulse). In one or more examples, the circumferential location of the electrode pairs on each emitter can be selected such that shock waves propagate in a particular direction with respect to the elongated tube (e.g., to promote interference between shock waves propagating in the same direction). In some examples, as shown in FIGS. 2A and 2B, the gap of the first electrode pair 262, 263 is circumferentially aligned (e.g., offset by zero degrees) with the gap of the second electrode pair 264, 265 relative to the elongated tube 204, such that both emitters generate shock waves at approximately the same radial direction with respect to the elongated tube 204. In some examples, in addition to the gap of the first electrode pair 262, 263 and the second electrode pair 264, 265 being spaced by a distance between 1 mm and 4 mm, the gap of the first electrode pair 262, 263 is circumferentially aligned with the gap of the second electrode pair 264, 265.

In some examples, the longitudinal distance and/or circumferential offset between adjacent emitters and their respective electrode pairs can be selected to produce a combined shock wave having a particular desired pressure increase over non-interfering shock waves (e.g., a pressure increase over shock waves produced from a single electrode pair, or shock waves produced from emitters spaced such that there is limited or no interference between the shock waves). For instance, the longitudinal distance between the spark gap of the first electrode pair 262 and the spark gap of the second electrode pair 264 can be selected such that a peak pressure of a combined shock wave is at least 1.25×, at least 1.5×, at least double (i.e., 2×), or at increments and gradients of relative increase within these values compared to a peak pressure of shock waves generated by a conventional shock wave catheter (e.g., a catheter having electrode pairs separated by a distance of 10 mm). The longitudinal distance and/or circumferential offset between adjacent emitters and their respective electrode pairs can also be selected to produce combined shock waves having double pressure waveforms, increased shear stress, increased mechanical stress, or some other beneficial attribute for treating calcified lesions.

Figure 3A:
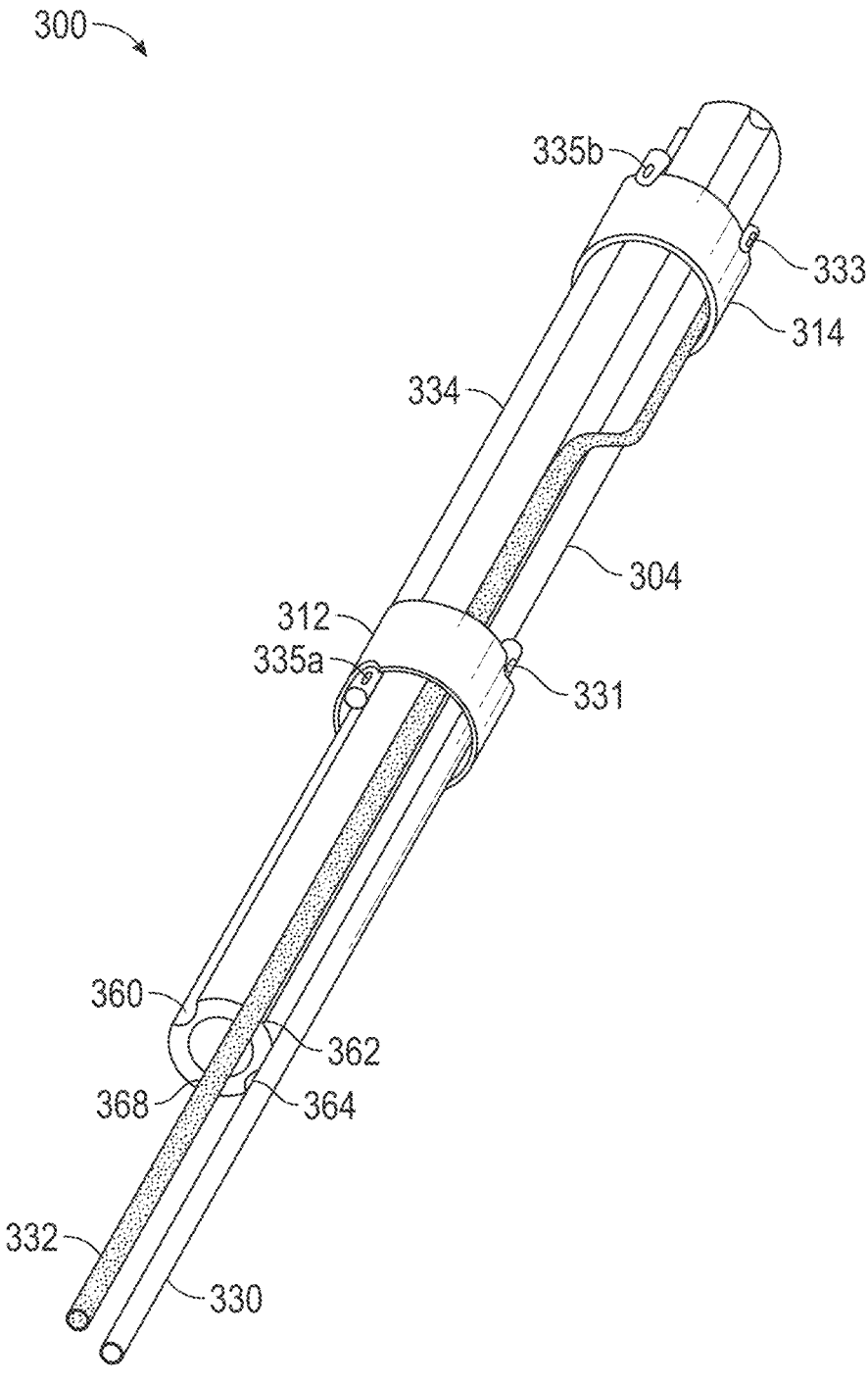
FIG. 3A illustrates an exemplary electrode assembly of a catheter, according to aspects of the present disclosure.
Figure 3B:
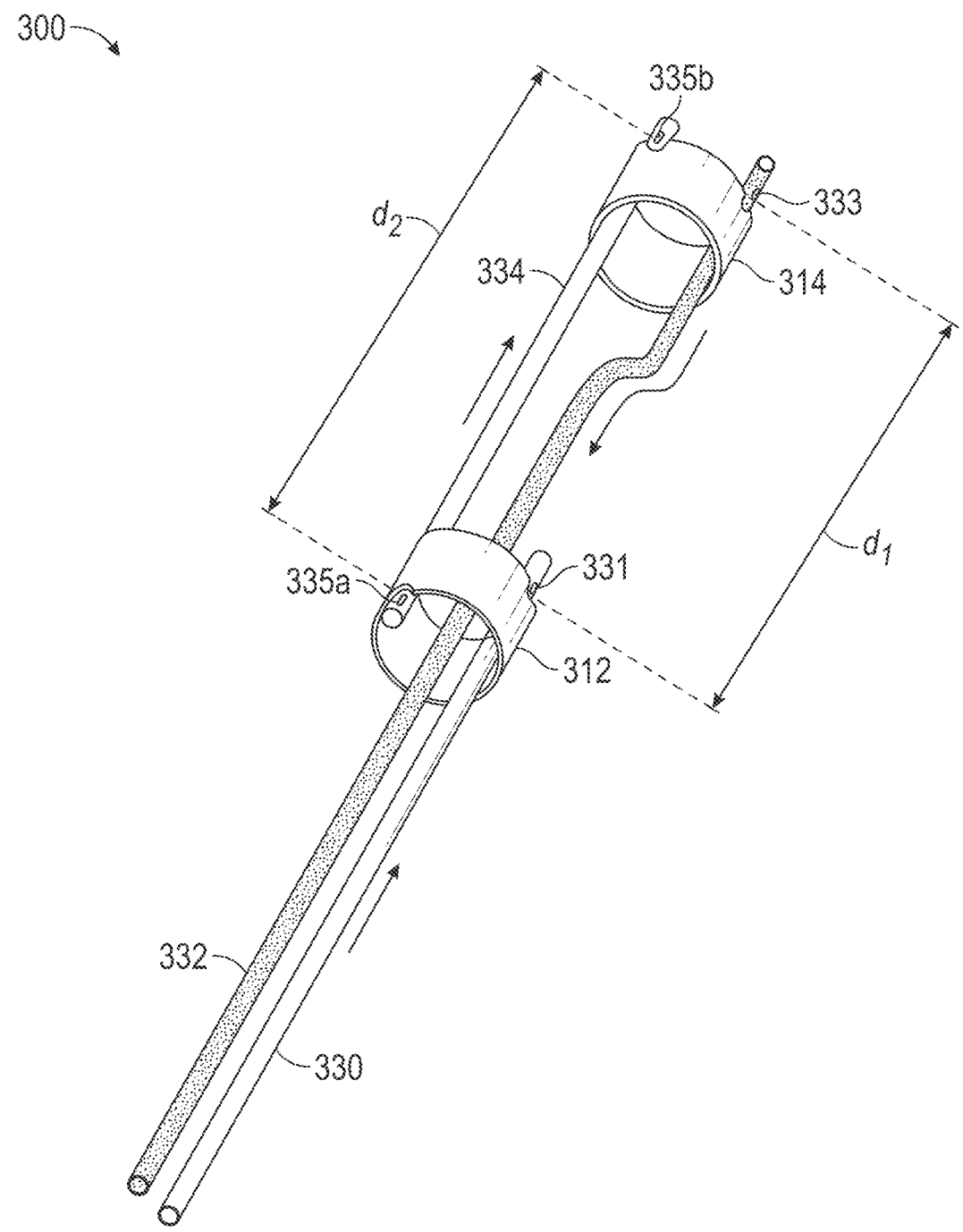
FIG. 3B illustrates the flow of current through the exemplary electrode assembly of FIG. 3A, according to aspects of the present disclosure.

FIGS. 3A-B provide a more detailed view of an exemplary electrode assembly 300 that can be included in a shock wave catheter, according to aspects of the disclosure. FIG. 3A provides a perspective view of the electrode assembly 300 disposed on an elongated tube 304 of a catheter. FIG. 3B provides an additional perspective view of the electrode assembly 300 without the elongated tube 304 to illustrate the connectivity and current flow through the electrode assembly 300.

As shown in FIG. 3A, an exemplary electrode assembly 300 can be implemented in a catheter that includes an elongated tube 304 having an outer surface that includes four longitudinal grooves 360, 362, 364, and 368. A number of insulated wires 330, 332, 334 are disposed on the outer surface of the elongated tube 304 extending along the grooves 360, 362, 364, 368. The electrode assembly 300 further includes a first conductive sheath 312 and a second conductive sheath 314, each sheath circumferentially mounted around the elongated tube 304.

As shown in FIG. 3A, each conductive sheath 312, 314 of electrode assembly 300 overlaps and surrounds at least a portion of the insulated wires 330, 332, 334. Each of the insulated wires 330, 332, 334 includes an electrically conductive portion 331, 333, 335a, 335b (e.g., an insulation removed portion of the wire) that is positioned near an edge of the conductive sheath to form a spark gap across which current can flow to generate a shock wave. For instance, a first insulated wire 330 may extend along the elongated tube 304 and have an electrically conductive portion 331 proximate to a first side edge of the first conductive sheath 312. A second insulated wire 332 may extend along the elongated tube 304 and have an electrically conductive portion 333 proximate to a first side edge of the second conductive sheath 314. A third insulated wire 334 may extend along the elongated tube 304 between the first conductive sheath 312 and the second conductive sheath 314, and include a first electrically conductive portion 335a proximate to a second side edge of the first conductive sheath 312 and a second electrically conductive portion 335b proximate to a second side edge of the second conductive sheath 314. In some examples, as shown in FIGS. 2A and 2B, the side edges of the conductive sheaths 312, 314 can include arcuate cut-outs or circular cut-outs in the conductive sheaths.

In the particular embodiment shown in FIGS. 3A and 3B, the electrode assembly 300 includes at least two emitters having at least two electrode pairs each, formed from the two conductive sheaths 312, 314 and the three insulated wires 330, 332, 334. More specifically, the first electrode pair includes an electrically conductive portion 331 of the first insulated wire 330 extending along the outer surface of the elongated tube and the first conductive sheath 312 mounted circumferentially around the elongated tube. The second electrode pair includes the first conductive sheath 312 and an electrically conductive portion 335a of a third insulated wire 334 extending along the outer surface of the elongated tube. The third electrode pair includes the second conductive sheath 314 and a further electrically conductive portion of the third insulated wire 335*b*. The fourth electrode pair includes an electrically conductive portion 333 of the second insulated wire 332 extending along the outer surface of the elongated tube and the second conductive sheath 314 mounted circumferentially around the elongated tube. The assembly of the elements of the first electrode pair and the second electrode pair (both formed from sheath 312) can be referred to as a first emitter, while the assembly of the elements of the third electrode pair and the fourth electrode pair (both formed from sheath 314) can be referred to as a second emitter.

FIG. 3B illustrates the flow of current through the exemplary electrode assembly. To initiate shock waves at the four electrode pairs of the electrode assembly, a high voltage pulse can be applied across the first insulated wire 330 and the second insulated wire 332 (e.g., using the high voltage pulse generator 150 of FIG. 1). When a high voltage pulse is applied across the first insulated wire 330 and the second insulated wire 332, a current may flow as indicated by the arrows, with the second insulated wire 332 as a common ground wire (i.e., connecting to a group or negative channel of the high voltage pulse generator). As shown, the current flows from the proximal end of the first insulated wire 330 toward the distal end of the insulated wire 330. The current then flows across a gap between the electrically conductive portion 331 of the first insulated wire 330 and the first conductive sheath 312 to generate a shock wave (e.g., a first shock wave corresponding to the first electrode pair). The current then flows around the first conductive sheath 312 and across a gap between the first conductive sheath 312 and an electrically conductive portion 335*a* of the third insulated wire 334 to generate a further shock wave (e.g., a second shock wave corresponding to the second electrode pair). As indicated, the current then flows from the proximal end of the third insulated wire 334 to the distal end of the third insulated wire 334. The current then flows across a gap between a further electrically conductive portion 335*b* of the third insulated wire 334 and the second conductive sheath 314 to generate a shock wave (e.g., a third shock wave corresponding to the third electrode pair). The current then flows around the second conductive sheath 314 and across a gap between the second conductive sheath 314 and an electrically conductive portion 333 of the second insulated wire 332 to generate a further shock wave (e.g., a fourth shock wave corresponding to the fourth electrode pair). The current then proceeds back in the proximal direction along the second insulated wire 332 (ground).

In one or more examples, longitudinally-adjacent electrode pairs of a pair of emitters in an electrode assembly are separated by a distance (see, e.g., distance "d" in FIGS. 2A and 2B). As shown in FIG. 3B, "$d_1$" measures the distance between the first electrode pair and the fourth electrode pair (a first pairing for constructive interference), while "$d_2$" measures the distance between the second electrode pair and the third electrode pair (a second pairing for constructive interference). As described previously, the distance between longitudinally-adjacent emitters can represent the distance between two electrode pairs of adjacent sheaths. In one or more examples, a first emitter and a second emitter are circumferentially aligned (e.g., wherein the gap of the an electrode pair of the first emitter is at the same circumferential location on the catheter as the gap of the an electrode pair of the second emitter) and separated by a distance between 1 mm and 4 mm, or between 3 mm and 3.5 mm, or at increments and gradients of distance within these values.

Two electrode pairs formed from the same conductive sheath (e.g., the first electrode pair and the second electrode pair both formed from the first conductive sheath 312) may be longitudinally separated by a similar or smaller longitudinal distance. However, in one or more examples, the two electrode pairs sharing a sheath may generate shock waves that do not interfere (or minimally interfere) with one another, such as because the electrode pairs are circumferentially offset from one another by an angle of 180 degrees (e.g., on opposite sides of catheter). Alternatively, the circumferential offset between two electrode pairs sharing a sheath may be selected to promote constructive interference, such as when the two electrode pairs are circumferentially offset from one another by an angle of less than 180 degrees, as will be discussed below.

Further, as described above, the distance between two electrode pairs (e.g., "$d_1$" or "$d_2$" in FIG. 3B) can designate the distance between a gap between electrodes of a first electrode pair on a first emitter (e.g., the gap between the insulation removed portion 331 of the first insulated wire 330 and the first conductive sheath 312 of the first emitter) and a gap between electrodes of a second electrode pair on a second emitter (e.g., the gap between the second conductive sheath 314 and an insulation removed portion 333 of the second insulated wire 332 of the second emitter). Alternatively, the distance between two electrode pairs may be approximated by the distance between a particular electrode of each emitter. For instance, the distance may be approximated by a distance between the insulation-removed portions of wire or conductive sheaths corresponding to electrodes of each emitter.

Figure 4A:
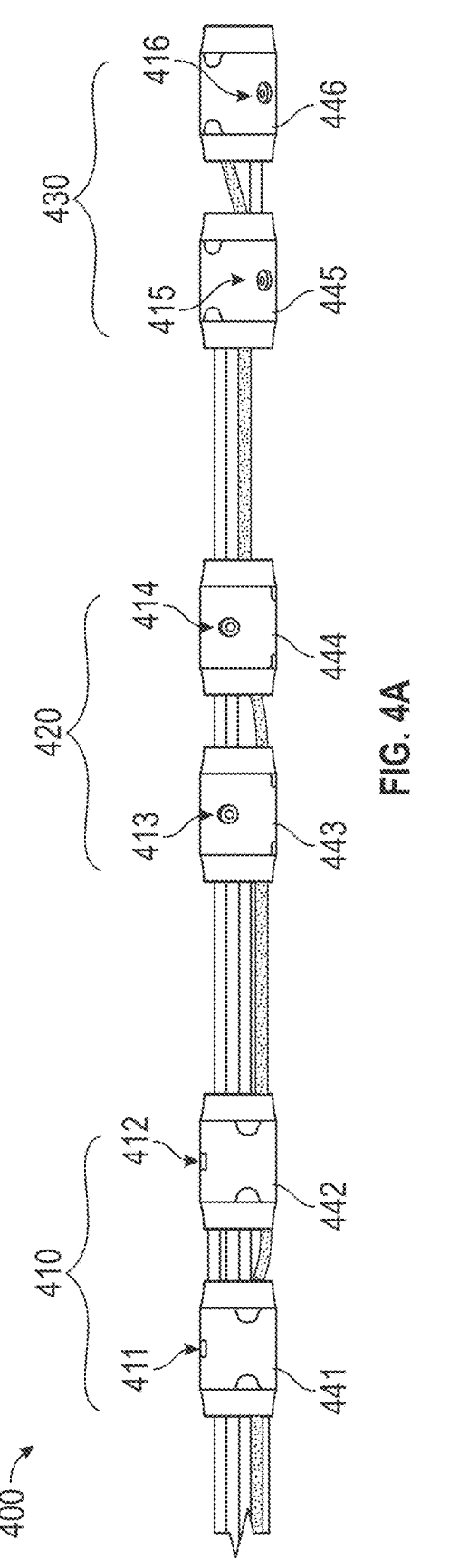
FIG. 4A illustrates a front side view of an exemplary electrode assembly having a proximal pair of emitters, a central pair of emitters, and a distal pair of emitters, according to aspects of the present disclosure.
Figure 4B:
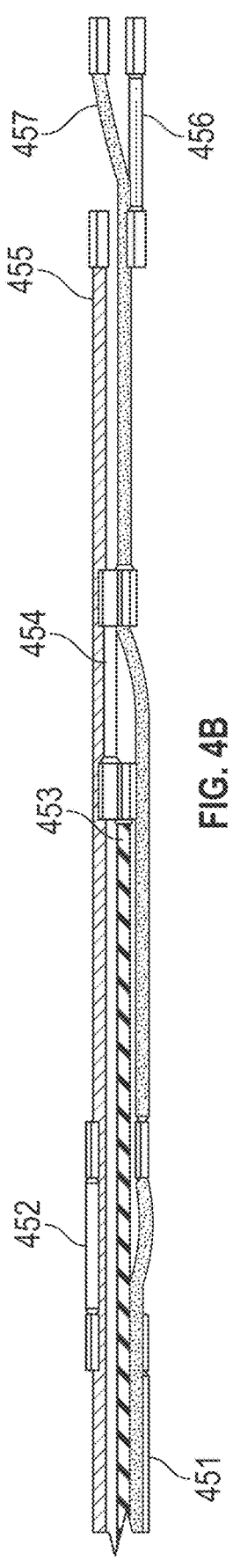
FIG. 4B illustrates the wiring of the exemplary electrode assembly of FIG. 4A, according to aspects of the present disclosure.
Figure 4C:
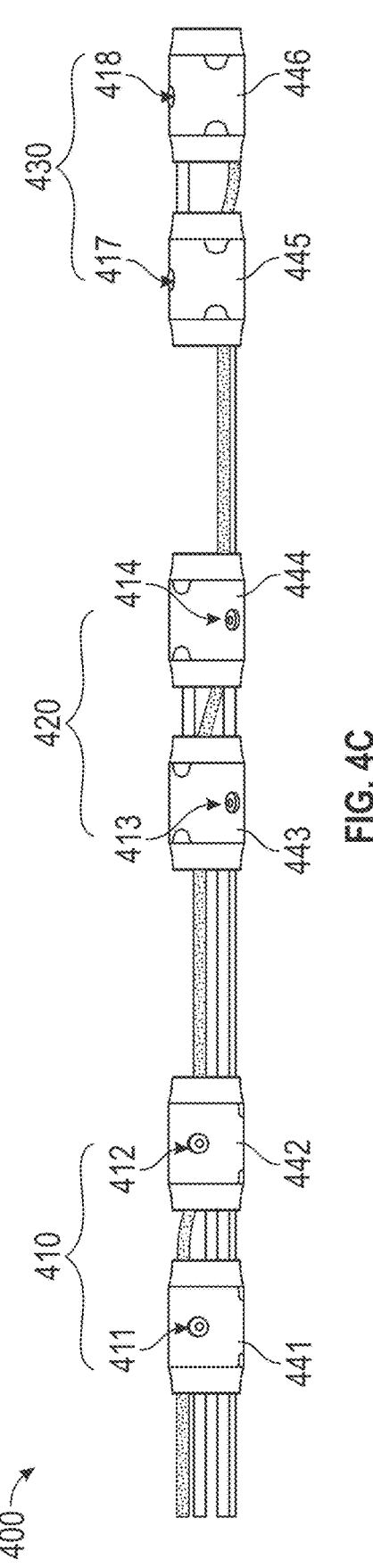
FIG. 4C illustrates a top side view of the exemplary electrode assembly of FIG. 4A, according to aspects of the present disclosure.
Figure 4D:
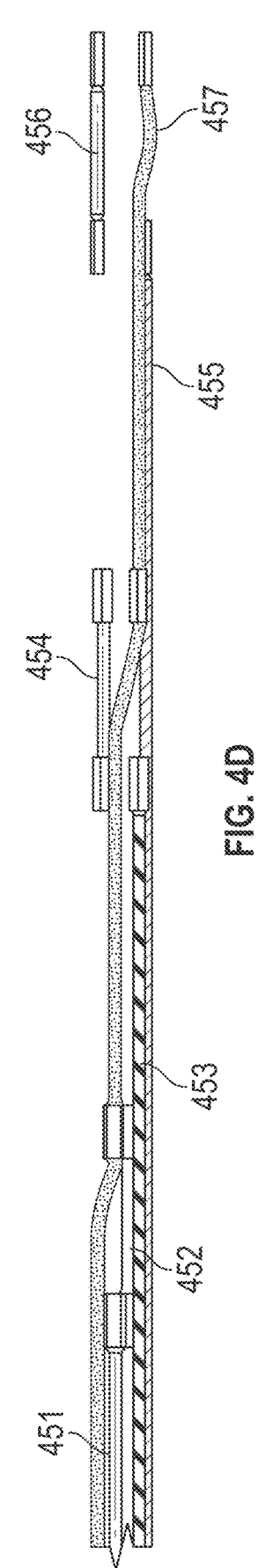
FIG. 4D illustrates a top side view of the exemplary electrode assembly wiring of FIG. 4B, according to aspects of the present disclosure.

While FIGS. 3A-B illustrate one exemplary electrode assembly formed from a first and second conductive sheath 312, 314 and three insulated wires 330, 332, 334, a catheter of the subject disclosure could be provided with any number of emitters for generating shock waves inside a flexible polymer enclosure. For instance, FIGS. 4A-D illustrate an exemplary electrode assembly 400 that can be included in a shock wave catheter, such as the exemplary catheter 100 shown in FIG. 1, according to aspects of the disclosure. The assembly includes three pairs of longitudinally-adjacent emitters configured as a respective proximal pair 410, a central pair 420, and a distal pair 430. FIG. 4A illustrates a front side view of the electrode assembly 400. FIG. 4B illustrates a front side view of the wiring of the electrode assembly 400 of FIG. 4A (i.e., a view of the assembly with the conductive sheaths 441, 442, 443, 444, 445, 446 removed to better depict the insulated wires 451, 452, 453, 453, 455, 456, and 457). FIG. 4C illustrates a top side view of the electrode assembly 400 shown in FIG. 4A (i.e., a view of the assembly rotated by 90 degrees to show additional features of the assembly 400). FIG. 4D illustrates a top side view of the wiring of the electrode assembly 400 (i.e., a view of the assembly of FIG. 4C with the conductive sheaths 441, 442, 443, 444, 445, 446 removed and/or the wiring of FIG. 4B rotated by 90 degrees).

As shown in FIGS. 4A and 4C, the exemplary electrode assembly 400 includes a plurality of conductive metal sheaths, more particularly a first conductive sheath 441, a second conductive sheath 442, a third conductive sheath 443, a fourth conductive sheath 444, a fifth conductive sheath 445, and a sixth conductive sheath 446. The exemplary electrode assembly 400 also includes a plurality of wires extending underneath and through the conductive sheaths, more particularly a first insulated wire 451, a second insulated wire 452, a third insulated wire 453, a fourth insulated wire 454, a fifth insulated wire 455, and a sixth insulated wire 456, and a common ground wire 457. The conductive sheaths 441, 442, 443, 444, 445, 446 and conductive portions of the insulated wires 451, 452, 453, 453, 455, 456 form a plurality of emitters that can be activated to produce shock waves at various locations along the electrode assembly 400.

As shown in FIGS. 4A and 4C, the conductive sheaths 441, 442, 443, 444, 445, 446 are arranged in closely-spaced (e.g., longitudinally-adjacent) pairs, such that shock waves generated by the emitter pairs formed from the longitudinally-adjacent sheaths can produce constructively interfering shock waves (i.e., combined shock waves). More specifically, the assembly 400 includes a proximal pair 410 including a first electrode pair 411 and a second electrode pair 412 formed from the respective first conductive sheath 441 and the second conductive sheath 442, a central pair 420 including a third electrode pair 413 and a fourth electrode pair 414 formed from the respective third conductive sheath 443 and the fourth conductive sheath 444, and a distal pair 430 including a fifth electrode pair 415 and a sixth electrode pair 416 formed from the respective fifth conductive sheath 445 and the sixth conductive sheath 446.

While the front view of the electrode assembly 400 of FIG. 4A shows each sheath (e.g., sheath 441 and sheath 442) having one electrode pair (e.g., electrode pair 411 and electrode pair 412), the electrode assembly 400 can include additional electrode pairs on the sheaths that are circumferentially offset from one another. For instance, FIG. 4C illustrates a top side view of the exemplary electrode assembly 400 of FIG. 4A, which reveals two additional electrode pairs on the distal emitter pair 430, specifically electrode pair 417 and electrode pair 418. In other words, electrode pairs 417 and 418 are circumferentially offset from the electrode pairs 415 and 416 of the sheaths 445 and 446, respectively. The proximal pair 410 and the central pair 420 can similarly include additional emitters (not shown) circumferentially offset around the first conductive sheath 441, the second conductive sheath 442, the third conductive sheath 443, and/or the fourth conductive sheath 444. For instance, the proximal pair 410 could include further electrode pairs (not shown) circumferentially offset approximately 180 degrees from the first electrode pair 411 and the second electrode pair 412 around the respective first conductive sheath 441 and the second conductive sheath 442. The central pair could also include further electrode pairs (not shown) circumferentially offset approximately 180 degrees from the third electrode pair 413, and the fourth electrode pair 414 around the respective third conductive sheath 443 and fourth conductive sheath 444. In one or more examples, the circumferential offset between electrode pairs on the same sheath can be less than 180 degrees, as will be discussed further below.

As discussed with respect to electrode assembly 200 of FIGS. 2A and 2B, the electrode pairs included in each of the proximal pair 410, the central pair 420, and the distal pair 430 may be substantially circumferentially aligned to promote constructive interference between shock waves generated by longitudinally-adjacent emitters of each pair. In one or more examples, and as shown in FIGS. 4A and 4C, the emitters and the respective electrode pairs of the proximal pair 410, the central pair 420, and the distal pair 430 may be positioned with different circumferential orientations to more evenly distribute shock wave treatments around the circumference of the catheter. For instance, as shown in FIG. 4A, the proximal pair 410 is oriented such that the first electrode pair 411 and the second electrode pair 412 are facing in a substantially upward direction. The emitters of the central pair 420 are circumferentially offset from the proximal pair 410, such that the third electrode pair 413 and the fourth electrode pair 414 generate combined shock waves in a different radial direction from the combined shock waves produced at the proximal pair 410. The electrode pairs of the distal pair 430 are circumferentially offset from both the proximal pair 410 and the central pair 420 to generate combined shock waves in a further different radial direction. The radial direction of shockwaves emitted from each pair of emitters can be selected such that the combination of the shock waves generated from the emitter pairs generates shock waves evenly around the circumference of a catheter. In some examples, and as shown in FIGS. 4A-D, a pair of constructively-interfering emitters may be circumferentially offset from another pair of emitters by approximately 30 degrees, approximately 60 degrees, approximately 120 degrees, or approximately 180 degrees, or at increments and gradients of degree within these values, around the circumference of a catheter. In other examples, the pairs of constructively-interfering emitters may be substantially circumferentially aligned (e.g., circumferentially offset by zero degrees), to produce combined shock waves in a particular radial direction with respect to a catheter.

FIGS. 4B and 4D illustrate the wiring of the electrode assembly 400. High voltage pulses can be applied across the insulated wires 451, 452, 453, 454, 455, 456 of the assembly to allow a user to selectively generate shock waves across certain emitters of the assembly 400. For instance, in the example shown in FIGS. 4A-D, each of the proximal pair 410, the central pair 420, and the distal pair 430 is separately wired to a voltage source (e.g., the high voltage pulse generator 150 of FIG. 1) to allow a user of the assembly 400 to selectively generate shock waves at either the proximal pair 410, the central pair 420, or the distal pair 430. A common ground wire 457 is provided to evacuate current from the electrode assembly 400.

As shown in FIGS. 4A-D, the proximal pair 410 includes a first insulated wire 451 extending between a voltage source and the first conductive sheath 441, and further includes a second insulated wire 452 extending between the first conductive sheath 441 and the second conductive sheath 442. Current flows from the proximal pair 410 via the common ground wire 457 having a conductive portion near the second conductive sheath 442. To generate shock waves at the proximal pair 410 (i.e., at the first electrode pair 411 and the second electrode pair 412 and any further electrode pair formed from the first and second conductive sheaths 441, 442), a high voltage pulse voltage can be applied to the first insulated wire 451.

The central pair 420 includes a third insulated wire 453 extending between a voltage source and the third conductive sheath 443, and further includes a fourth insulated wire 454 extending between the third conductive sheath 443 and the fourth conductive sheath 444. Current flows from the central pair 420 via the common ground wire 457 having a conductive portion near the fourth conductive sheath 444. To generate shock waves at the central pair 420 (i.e., at the third electrode pair 413 and the fourth electrode pair 414 and any further electrode pair formed from the third and fourth conductive sheaths 443, 444), a high voltage pulse voltage can be applied to the third insulated wire 453.

The distal pair 430 includes a fifth insulated wire 455 extending between a voltage source and the fifth conductive sheath 445, and further includes a sixth insulated wire 456 extending between the fifth conductive sheath 445 and the sixth conductive sheath 446. Current flows from the distal pair 430 via the common ground wire 457 having a conductive portion near the sixth conductive sheath 446. To generate shock waves at the distal pair 430 (i.e., at the fifth electrode pair 415 and the sixth electrode pair 416 and any further electrode pair formed from the fifth and sixth conductive sheaths 445, 446), a high voltage pulse voltage can be applied to the fifth insulated wire 455.

While the exemplary catheter 100 shown in FIG. 1 and the electrode assemblies of FIGS. 4A-C include three pairs of emitters that can be activated to generate combined shock waves at three locations along the length of the catheter, any number of electrode assemblies and/or emitters can be included in a catheter without departing from the scope of the present disclosure, as described below. For instance, some exemplary catheters include a single pair of longitudinally-adjacent emitters configured to generate combined shock waves at a single location along a catheter. Further exemplary catheters could include two pairs, three pairs, four pairs, or an even greater number of pairs, each pair including one or more constructively-interfering emitters spaced to generate combined shock waves along the length of a catheter. Alternatively or in addition, exemplary catheters could include groups of three or four emitters that are constructively-interfering emitters spaced to generate combined shock waves along the length of a catheter. Alternatively or in addition to longitudinally-adjacent emitters configured to generate shock waves that constructively interfere to form a combined shock wave, catheters comprising circumferentially-adjacent (e.g., electrode pairs circumferentially offset from one another by angle of less than 180 degrees) electrode pairs configured to generated shock waves that constructively interfere to form a combined shock wave are also contemplated by this disclosure, as will be discussed below.

Figure 5:
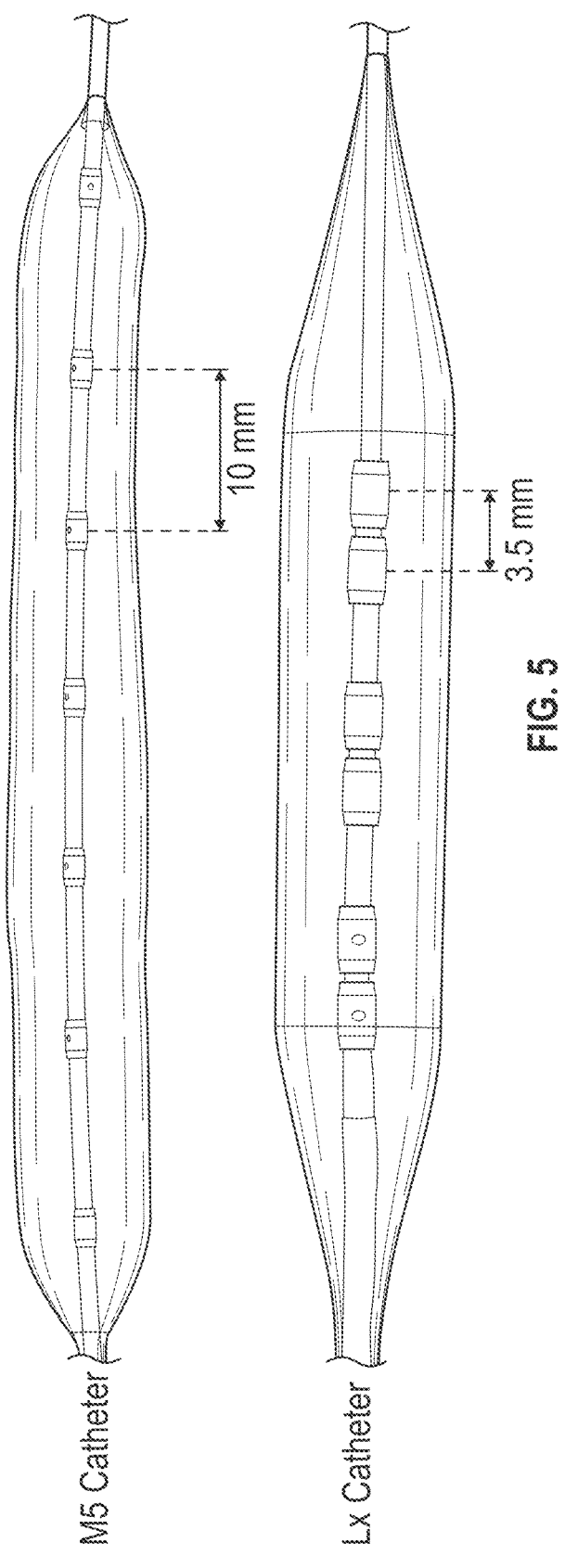
FIG. 5 provides images of exemplary shock wave catheters, according to aspects of the present disclosure.

FIG. 5 provides two images of exemplary shock wave catheters including aspects of the disclosure. The top image shows an exemplary "M5" catheter having five emitters spaced apart by approximately ten millimeters (10 mm). The bottom image shows an exemplary "Lx" catheter having six adjacent emitters arranged in pairs, with each emitter in the pair spaced apart from the other emitter of the pair by approximately 3.5 mm. As shown in FIG. 5, the emitters of the M5 catheter are evenly spaced at a distance of 10 mm along the length of the catheter. The emitters of the Lx catheter are arranged in longitudinally-adjacent pairs, and more specifically in a proximal pair, a central pair, and a distal pair. The longitudinally-adjacent emitters of each of the respective proximal, central, and distal pairs are spaced approximately 3.5 mm apart to promote constructive interference between shock waves generated at longitudinally-adjacent emitters of a pair. As shown in FIG. 5, the distance between the proximal pair and the central pair and the distance between the central pair and the distal pair is greater than 3.5 mm.

Figure 6:
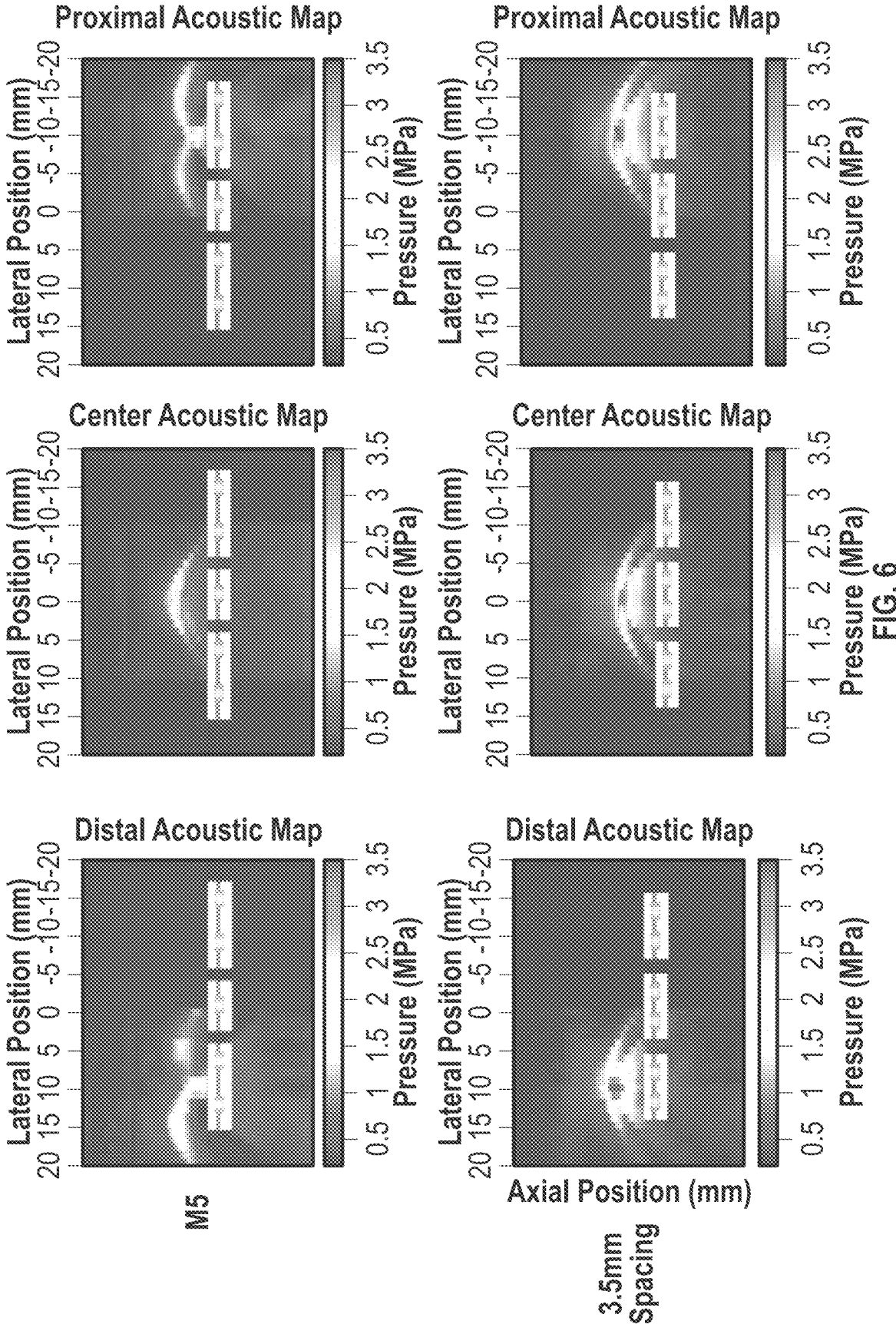
FIG. 6 provides a series of heat-map graphics illustrating the pressure of acoustic wavefronts generated by exemplary catheters as shown in FIG. 5, according to aspects of the present disclosure.

FIG. 6 provides a series of heat-map graphics depicting the acoustic pressure wavefronts of shock waves generated by various exemplary catheters generated by exemplary catheters as shown in FIG. 5. The x-axis of each graph (at the top of each image) corresponds to the lateral position along the catheter of the pressure reading, where "0" represents a central location along the electrode array of the catheter (e.g., a location of a central emitter of the catheter). The shock waves generated by the catheters at each respective lateral position are delineated by the increased pressure regions represented by the lighter shading areas according to the pressure scale beneath each graphic.

The spacing of the emitters along the catheter is indicated with a schematic superimposed over each heat-map. The top row of graphics provides pressure readings from a commercially available M5 catheter from Shockwave Medical, Inc.

The M5 catheter includes an array of emitters, with adjacent emitters spaced approximately 10 mm apart along the length of the catheter that are not uniformly circumferentially aligned relative to one another. In greater detail, viewed left-to-right, the first two emitters are aligned with each other, then there is a rotational offset after which the next two emitters are aligned with each other, then there is a further rotational offset and the last emitter is not aligned with any of the other emitters. The bottom row of graphs provides pressure readings from an exemplary Lx catheter implementing aspects of the present disclosure (the "3.5 mm Spacing" catheter). The Lx catheter includes a proximal pair of two longitudinally-adjacent emitters, a central pair of two longitudinally-adjacent emitters, and a distal pair of two longitudinally-adjacent emitters. Within each of the proximal, central, and distal pairs, adjacent emitters are spaced apart at a distance of approximately 3.5 mm and where the pairs of adjacent emitters are circumferentially aligned relative to one another. For the paired emitters, in relation to each other, viewed left-to-right, the first two (proximal) emitters are aligned with each other, then there is a rotational offset after which the next two (central) emitters are aligned with each other, then there is a further rotational offset after which that last two emitters (distal) are aligned with each other.

As shown in FIG. 6, when the emitters of the 3.5 mm spacing Lx catheter are activated, the acoustic pressure wavefronts (i.e., shock waves) produced at longitudinally-adjacent emitters converge to create double or multiple wavefronts and regions of highly focused, high amplitude pressure waves (i.e., a combined shock wave), depicted by the double-hump of lighter shading areas that overlap one another at the lateral positions corresponding to each longitudinally-adjacent pair of emitters. In contrast, the acoustic pressure wavefronts produced by the M5 catheter do not converge or converge only minimally, depicted by the lighter shading areas that are largely adjacent one another with minimal overlap at the lateral positions corresponding to each emitter, resulting in relatively more diffuse lower-pressure wavefronts. As a result, the 3.5 mm spacing Lx catheter can produce acoustic wavefronts having increased pressure compared to the pressure of acoustic wavefronts produced by the M5 catheter.

Figure 7:
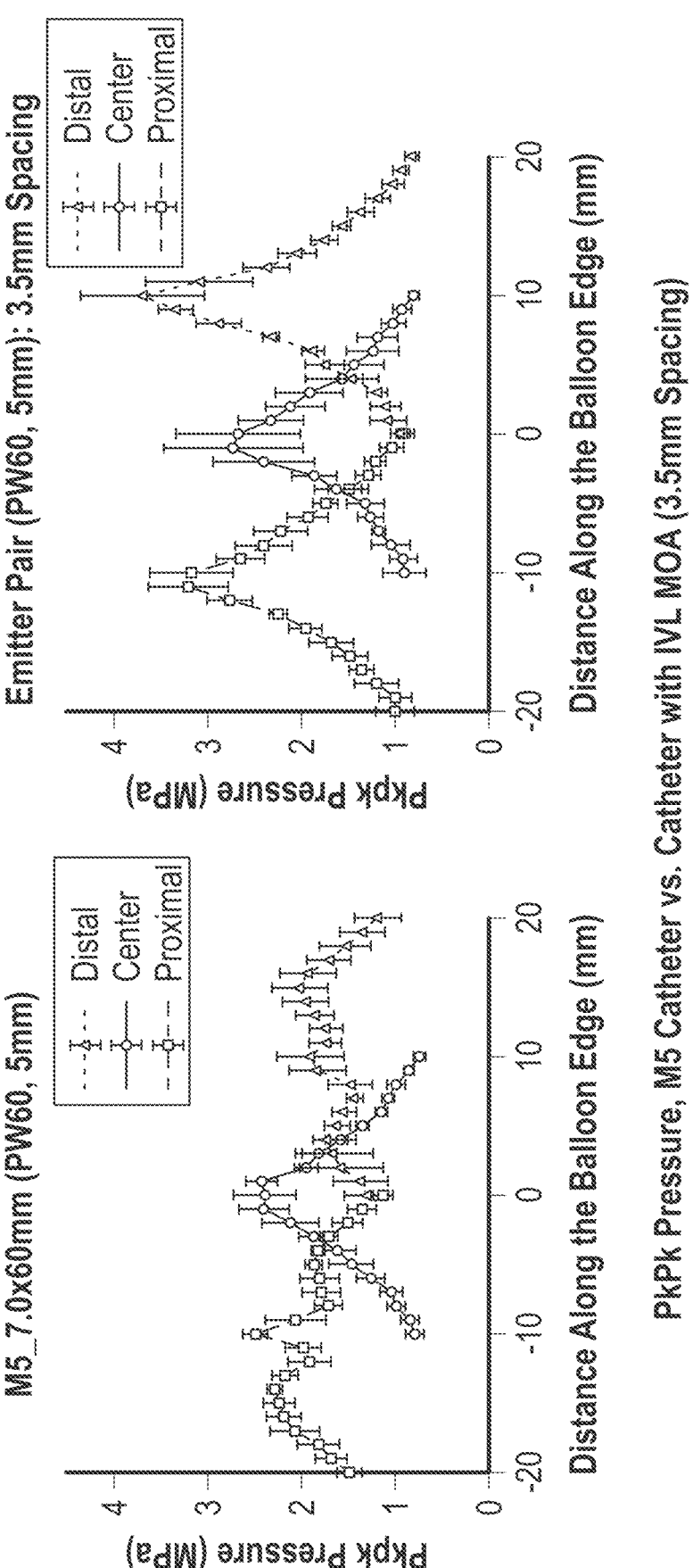
FIG. 7 provides two graphs illustrating the pressure of acoustic wavefronts measured along the balloon edge of exemplary catheters, according to aspects of the present disclosure.

FIG. 7 provides two graphs displaying pressure readings of shock waves produced by exemplary catheters, according to aspects of the present disclosure. The x-axis corresponds to the lateral distance of the pressure reading along the edge of an angioplasty balloon (i.e., along the surface of a flexible polymeric enclosure of a catheter), where "0" represents a central position on the balloon. The left side graph shows the peak-to-peak pressure readings along the length of an M5 catheter having emitters spaced apart by approximately 10 mm (e.g., the M5 catheter described above in relation to FIGS. 5 and 6). The right side graph shows the peak-to-peak pressure readings along the length of a catheter having pairs of longitudinally-adjacent emitters spaced at approximately 3.5 mm (e.g., the Lx catheter described above in relation to FIGS. 5 and 6). FIG. 7 provides an average pressure of three datasets, while FIG. 6 shows an exemplary pressure reading from a single representative data sample. As shown in FIG. 7, the 3.5 mm spacing Lx catheter produces acoustic shock waves having an increased peak pressure compared to the shock waves produced by the M5 catheter.

Figure 8:
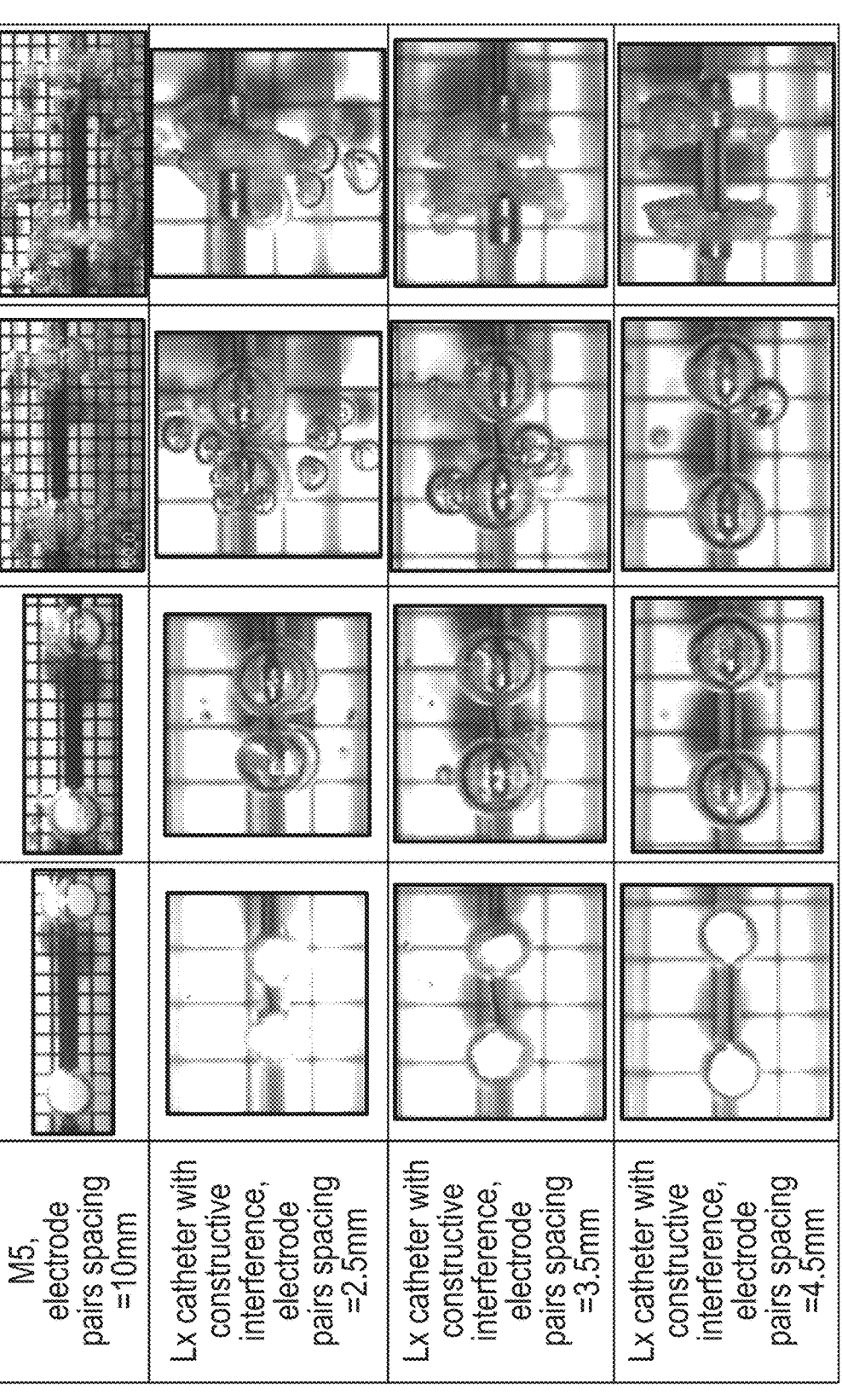
FIG. 8 provides a series of images of the formation and collapse of bubbles resulting from the activation of emitters of exemplary catheters, according to aspects of the present disclosure.

FIG. 8 provides a series of images of bubble progression at a pair of emitters of four exemplary catheters responsive to high voltage pulses applied across the emitters, according to aspects of the present disclosure. The top row of images shows bubble formation, expansion, and collapse by an M5 catheter having a pair of emitters spaced apart by a distance of 10 mm. The second, third, and fourth rows of images show bubble formation, expansion, and collapse by exemplary Lx catheters implementing aspects of the subject disclosure having longitudinally-adjacent emitters spaced apart at a distance of 2.5 mm, 3.5 mm, and 4.5 mm, respectively. As shown in FIG. 8, the M5 catheter produces bubbles that expand and collapse independently to produce two smaller acoustic shock waves in the conductive fluid. As the spacing between the emitters decreases in the exemplary Lx catheters, the bubbles begin to converge and overlap to produce a single combined acoustic shock wave. For instance, while the bubbles produced by the 10 mm spacing M5 catheter do not interfere, the bubbles produced by the 4.5 mm spacing Lx catheter do not interfere or interfere only minimally, and the bubbles produced by the 3.5 mm and 2.5 mm spacing Lx catheters interfere (i.e., expand and collapse together) to produce a combined shock wave.

Figure 9:
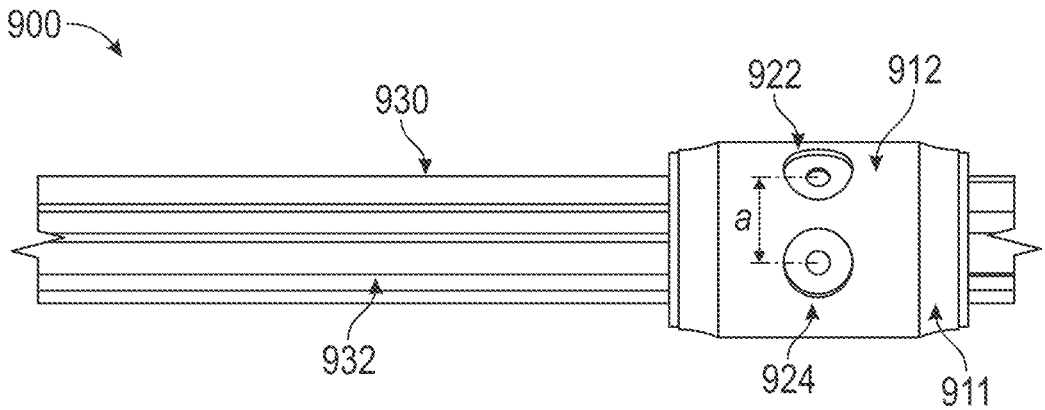
FIG. 9 illustrates an exemplary electrode assembly having a pair of electrode pairs at the same longitudinal location but circumferentially offset from one another by 60 degrees, according to aspects of the present disclosure.

As discussed above, alternatively or additionally to having longitudinally-spaced electrode pairs (e.g., located on separate sheaths of an emitter pair), a catheter can include multiple electrode pairs on the same sheath that are circumferentially offset from one another. FIG. 9 illustrates an exemplary catheter electrode assembly 900 having a pair of electrode pairs 922, 924 at the same longitudinal location on the catheter but circumferentially offset from one another by 60 degrees.

As shown, the electrode pairs 922, 924 of the electrode assembly 900 can be formed from a conductive sheath 912 and a number of wires 930, 932. In one or more examples, the electrode pairs 922, 924 can be formed from circular cut-outs (as shown in FIG. 9 and like the electrode assembly 200 of FIG. 2A) and/or arcuate cut-outs (as shown in FIG. 2B) in the sheath 912. When voltage is applied to the electrode assembly 900, current flows between the cut-outs of the conductive sheath (a first electrode) and an electrically conductive portion of an insulated wire (a second electrode) (e.g., an insulation removed portion of a wire) to generate shock waves. In one or more examples, an insulation sheath 911 can be positioned between the electrically conductive portions of the wires and the cut-outs to prevent unintended current flow between the conductive portions of the wires and the conductive sheaths, providing the path through which current can flow between the electrodes of each electrode pair.

As shown in FIG. 9, the first electrode pair 922 is circumferentially offset by an angle "a" from the second electrode pair 924. The electrode pairs 922 and 924 are arranged in a closely-spaced (e.g., circumferentially-adjacent) pair such that shock waves generated by each electrode pair can constructively interfere with one another to create a combined shock wave. The specific degree of the circumferential offset a between the emitters can be varied. For instance, rather than being offset by 60 degrees, the electrode pairs 922 and 924 can be circumferentially offset from one another by 30 degrees, 90 degrees, 120 degrees, 140 degrees, 160 degrees, or at increments and gradients of degree within these values.

Figure 10:
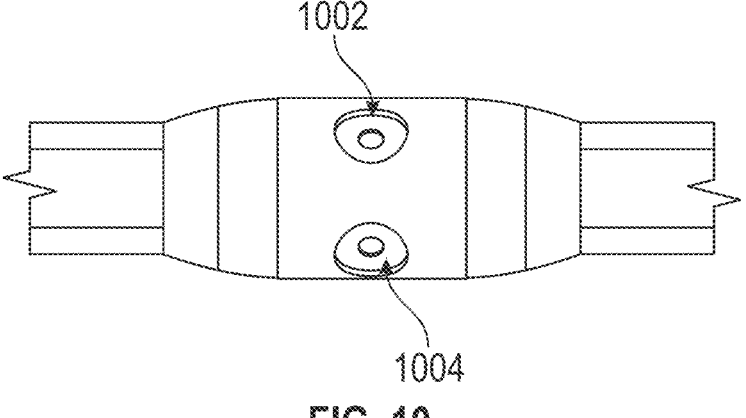
FIG. 10 provides an image of an exemplary shock wave catheter with an electrode assembly having a pair of electrode pairs at the same longitudinal location but circumferentially spaced apart from one another by 60 degrees, according to aspects of the present disclosure.

FIG. 10 provides an image of an exemplary shock wave catheter with a catheter electrode assembly having a pair of electrode pairs, 1002 and 1004, at the same longitudinal location on a catheter but circumferentially offset from one another by approximately 60 degrees.

Figure 11:
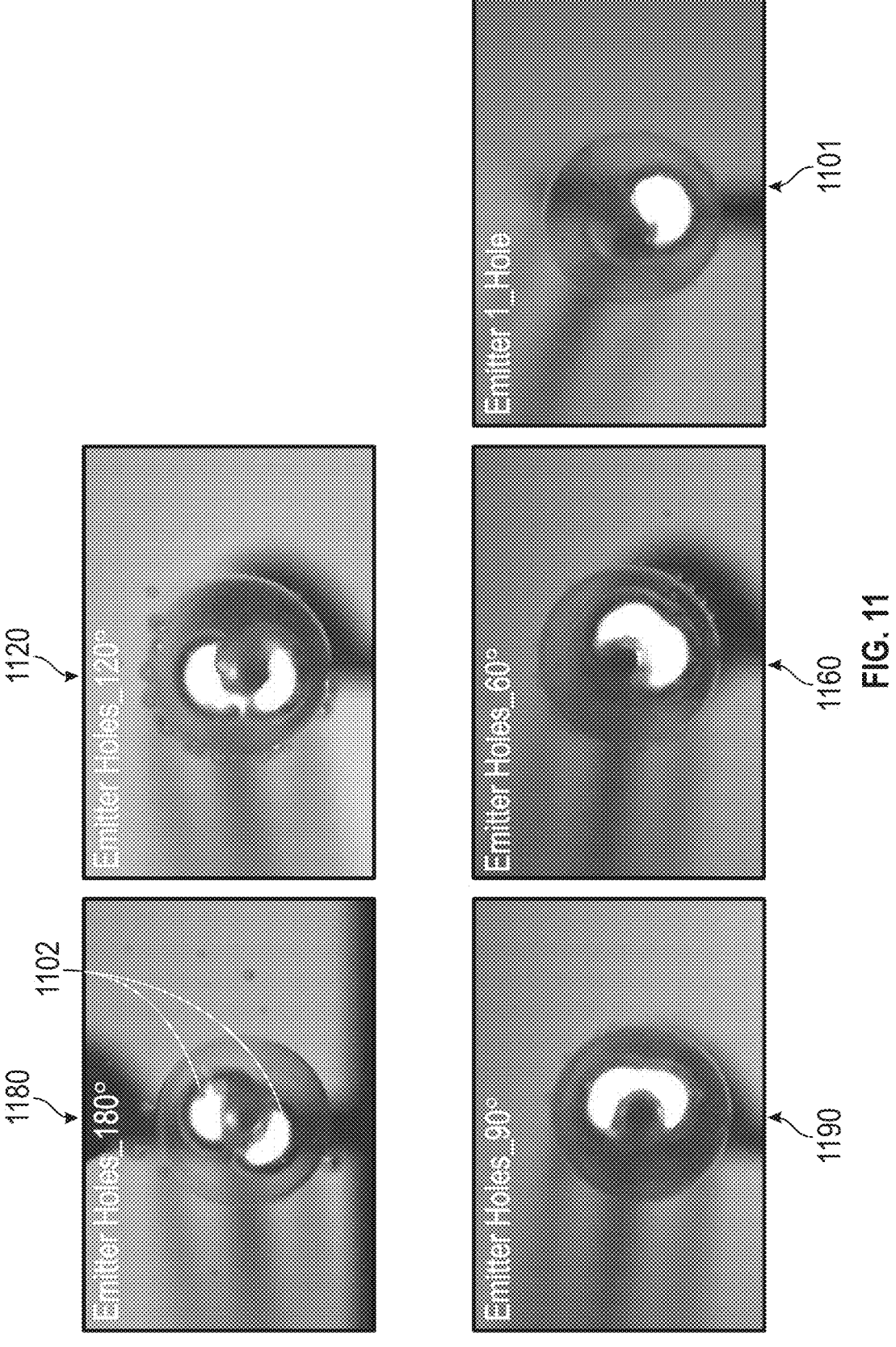
FIG. 11 provides a series of images of the formation and collapse of bubbles resulting from the activation of exemplary catheters, according to aspects of the present disclosure.

FIG. 11 provides a series of images of the formation and collapse of bubbles resulting from the activation of an exemplary shock wave catheter with an electrode assembly having a pair of electrode pairs (referred to within the figure as "emitter holes") at the same longitudinal location but circumferentially offset from one another by 180 degrees, 120 degrees, 90 degrees, 60 degrees, and 0 degrees. More specifically, image 1180 corresponds to the offset of 180 degrees, image 1120 corresponds to the offset of 120 degrees, image 1190 corresponds to the offset of 90 degrees, image 1160 corresponds to the offset of 60 degrees, and image 1101 corresponds to an offset of 0 degrees (i.e., where 0 degrees is an emitter with only one electrode pair, provided as a control example).

As shown in image 1180, the bubbles 1102 generated by each electrode pair when offset by 180 degrees from one another do not interfere with one another. Accordingly, there is little to no constructive interference between shock waves generated by electrode pairs offset by 180 degrees relative to one another. In comparison, as shown in images 1120, 1190, and 1160, the bubbles generated by each electrode pair when offset by 120 degrees, 90 degrees, and 60 degrees, from one another begin to merge together into one combined bubble. Thus, when offset by any of these degrees (e.g., 120 degrees, 90 degrees, 60 degrees), there is constructive interference between the bubbles generated by the emitters which tends to create a combined bubble.

Figure 12:
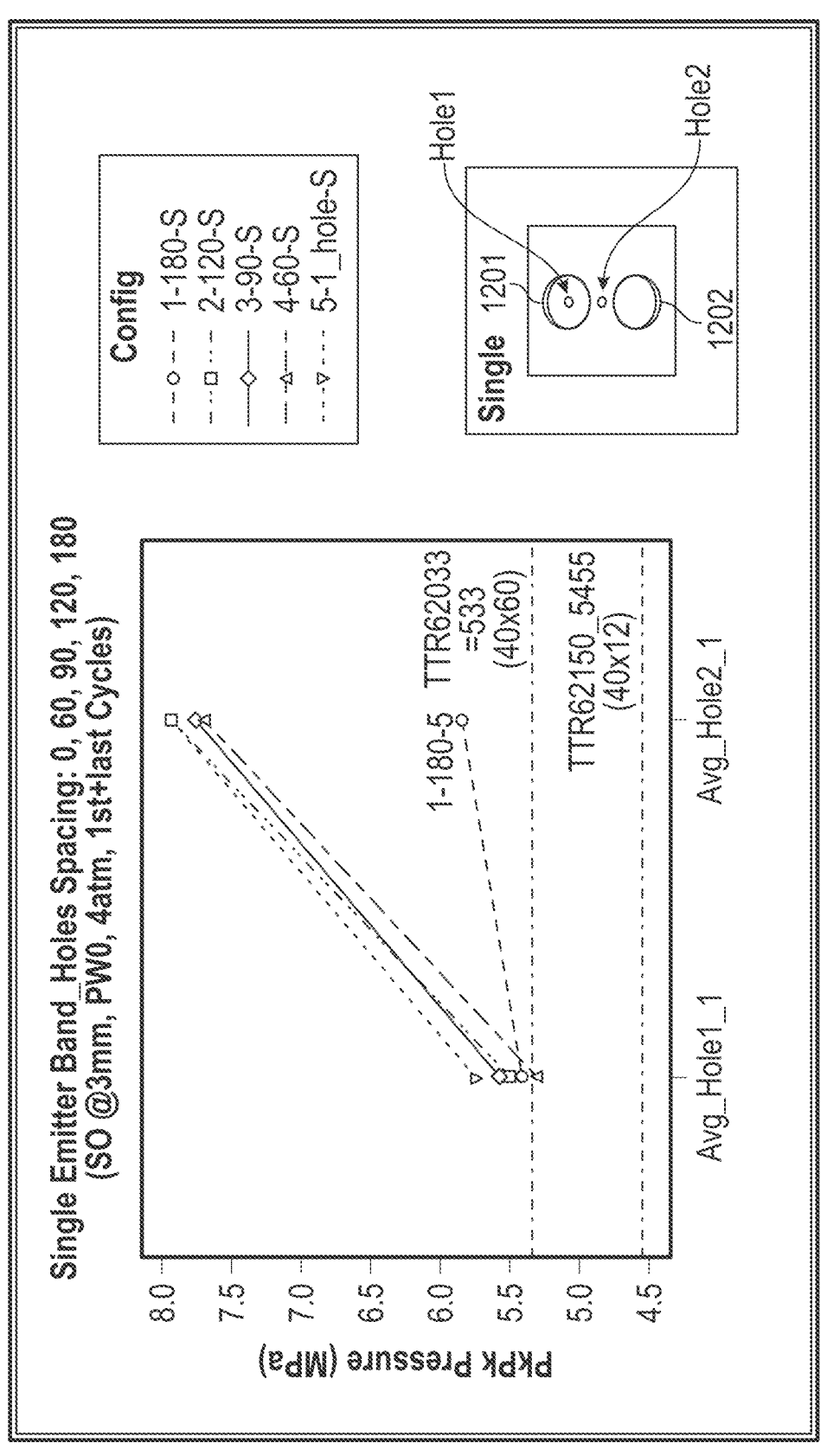
FIG. 12 provides a graph illustrating the pressure of acoustic wavefronts from a single emitter measured along the balloon edge of exemplary catheters, according to aspects of the present disclosure.

FIG. 12 provides a graph illustrating the pressure of acoustic wavefronts from a single emitter measured along the balloon edge of an exemplary catheter with an electrode assembly having two electrode pairs, 1201, 1202 at the same longitudinal location but circumferentially spaced apart from one another by 180 degrees, 120 degrees, 90 degrees, 60 degrees, and 0 degrees, according to aspects of the present disclosure. The pressure values shown in the graph of FIG. 12 are tabulated in Table 1 below.

TABLE 1

| Single Emitter, Pressure values of two longitudinally aligned and circumferentially offset electrode pairs | | |
|---|---|---|
| | Measurement Location | |
| Offset Degree | Center of Electrode Pair 1 (1201) | Centered between Electrode Pair 1 (1201) and Electrode Pair 2 (1202) |
| 180 degrees | ~5.4 MPa | ~5.8 MPa |
| 120 degrees | ~5.5 MPa | ~7.9 MPa |
| 90 degrees | ~5.6 MPa | ~7.7 MPa |
| 60 degrees | ~5.33 MPa | ~7.6 MPa |
| 0 degrees | ~5.8 MPa | NA |

As shown in the images of FIG. 11, when locating a pair of electrode pairs at the same longitudinal location but circumferentially offset from one another by less than 180, the shock waves generated by the emitters tend to constructively interfere with one another to create a combined bubble. Moreover, as shown in the graph of FIG. 12 and Table 1, locating a pair of electrode pairs at the same longitudinal location but circumferentially offset from one another by less than 180 also tends to result with greater pressure values when measured between the electrode pairs (such as where the combined bubble may form). Accordingly, electrode assemblies with electrode pairs located at the same longitudinal location and offset by less than 180 degrees, such as the electrode assembly of FIG. 9, can realize greater pressure values than an electrode assembly with electrode pairs offset from one another by 180 degrees.

Figures 13A, 13B:
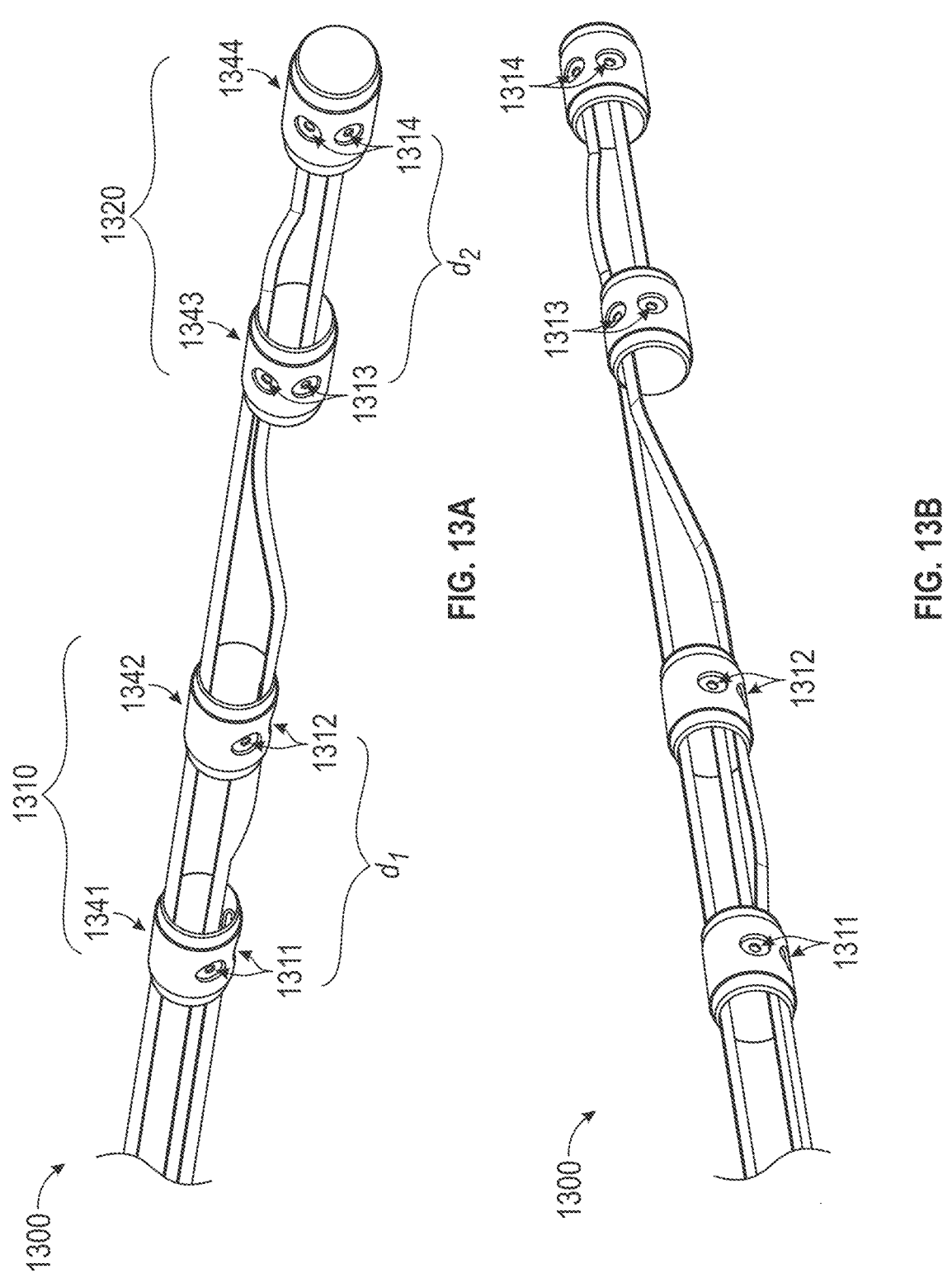
FIG. 13A illustrates a front right view of an exemplary electrode assembly for a catheter having a plurality of pairs of emitters spaced apart along the length of the catheter.
FIG. 13B illustrates a front left view of the exemplary electrode assembly of FIG. 13A.

In addition to locating two electrode pairs at the same longitudinal location, such as on the same sheath, a catheter can include multiple pairs of electrode pairs located adjacent one another, e.g., multiple sheaths spaced along the length of the catheter. FIGS. 13A-B illustrate an exemplary electrode assembly 1300 having a plurality of pairs of longitudinally aligned emitters spaced along the length of the catheter, according to aspects of the present disclosure. FIG. 13A illustrates a front right view of the exemplary electrode assembly, and FIG. 13B illustrates a front left view. Relative to the exemplary electrode assembly 400 of FIGS. 4A-C, the electrode assembly 1300 differs in that here the longitudinally aligned electrode pairs (e.g., those located on the same sheath) are circumferentially offset by less than 180 degrees relative to one another.

The sheaths and electrode pairs of the electrode assembly 1300 are connected by a number of wires, which can be arranged similarly to the wiring described with reference to FIGS. 3A-B and 4A-C. The emitters of the electrode assembly 1300 can be formed from a conductive sheath with circular cut-outs (like the electrode assembly 200 shown in FIG. 2A) and/or arcuate cut-outs (as shown in FIG. 2B). When voltage is applied to the electrode assembly, current flows between the cut-outs of the conductive sheath (a first electrode) and an electrically conductive portion of an insulated wire (a second electrode) (e.g., an insulation removed portion of a wire) to generate shock waves. An insulation sheath can be positioned between the electrically conductive portions of the wires and the cut-outs to prevent unintended current flow between the conductive portions of the wires and the conductive sheaths, providing the path through which current can flow between the electrodes of each emitter.

As shown in FIG. 13A, the electrode assembly 1300 includes a first pair 1310 of longitudinally-adjacent sheaths 1341 and 1342 (emitters), with each sheath containing a pair of longitudinally aligned but circumferentially offset electrode pairs 1311, 1312, as well as a second pair 1320 of longitudinally-adjacent sheaths 1343 and 1344 (emitters) that each contain a pair of longitudinally aligned but circumferentially offset electrode pairs 1313 and 1314.

The conductive sheaths 1341, 1342, 1343 and 1344 are arranged in closely-spaced (e.g., longitudinally-adjacent) emitter pairs 1310 and 1320 such that shock waves generated by the electrode pairs of each sheath can constructively interfere with the shock waves generated by the longitudinally-adjacent sheath. For example, the shock waves generated by the electrode pairs 1311 of sheath 1341 can constructively interfere with the shock waves generated by the electrode pairs 1312 of sheath 1342. As explained above with respect to FIG. 9, longitudinally aligned and circumferentially offset electrode pairs, such as those of the same sheath, can also constructively interfere with one another. Thus, in one or more examples, the shock waves generated by the separate electrode pairs 1311 of sheath 1341 constructively interfere with one another to generate a first combined shock wave bubble, the shock waves generated by the separate electrode pairs 1312 of sheath 1342 constructively interfere with one another to generate a second combined shock wave bubble, and then those first and second combined shock wave bubbles will constructively interfere with one another based on their close longitudinal spacing to form one combined shock wave from the emitter pair 1310.

With respect to the first emitter pair 1310, the sheath 1341 is longitudinally separated from sheath 1342 by distance $d_1$, and the electrode pairs 1311 of sheath 1341 are circumferentially aligned with the electrode pairs 1312 of sheath 1342. Similarly, in the second emitter pair 1320, the sheath 1343 is longitudinally separated from the sheath 1344 by distance $d_2$, with the electrode pairs 1313 of the sheath 1343 circumferentially aligned with the electrode pairs 1314 of sheath 1344. As used to describe the electrode assembly 1300 of FIG. 13A, $d_1$ and $d_2$ designate the distance between longitudinally-adjacent sheaths of a pair. These distances can also describe the distance between emitters of those sheaths, for instance, the distance between electrode pairs 1311 and electrode pairs 1312, and/or distance between spark gaps of electrode pairs 1311 and spark gaps of electrode pairs 1312 (e.g., the gaps across which current jumps to generate a shock wave when voltage is applied to the electrodes of each emitter). The distance $d_1$ that separates the sheaths 1341 and 1342 can be equal to, less than, or greater than, the distance $d_2$ that separates the sheaths 1343 and 1344. In one or more examples, the distances between sheaths of a pair can be between 1 mm and 4 mm, or at increments and gradients of distance within these values. In one or more examples, the distance between sheaths of a pair is 3.5 mm.

As shown in FIG. 13A, the emitters of the first pair 1310 are not circumferentially aligned with the emitters of the second pair 1320 (e.g., electrode pairs 1311 and 1312 are located at a different circumferential location on the catheter from the electrode pairs 1313 and 1314). The radial direction of shockwaves emitted from each emitter pair (e.g., 1310 and 1320) can be selected such that the combination of the shock waves generated from the emitters of the pairs generates shock waves evenly around the circumference of a catheter. In some examples, and as shown in FIGS. 13A-B, the emitter pair 1310, which includes constructively-interfering electrode pairs 1311 and 1312, is circumferentially offset from emitter pair 1320. In one or more examples, the offset between emitter pairs 1310 and 1320 can be approximately 30 degrees, approximately 60 degrees, approximately 120 degrees, or approximately 180 degrees, or at increments and gradients of degree within these values, around the circumference of a catheter. In one or more examples, each pair of emitters with their respective electrodes, (e.g., electrode pairs 1311, 1312, 1313, and 1314) can be circumferentially aligned with one another. That is, the emitter pairs 1310 and 1320 may be substantially circumferentially aligned (e.g., circumferentially offset by zero degrees), to produce combined shock waves in a particular radial direction with respect to a catheter.

Figure 14:
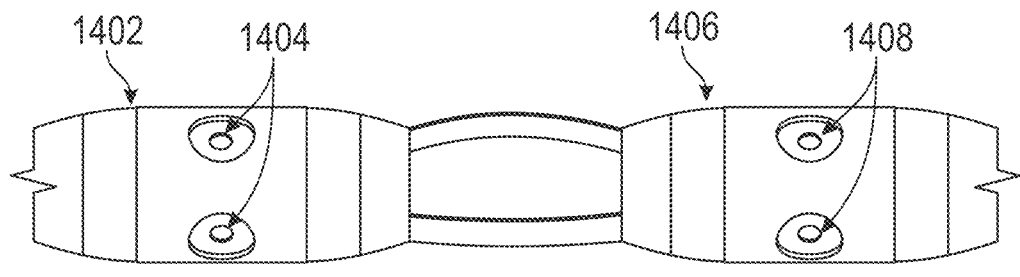
FIG. 14 provides an image of an exemplary shock wave catheter with a first emitter that has a pair of electrode pairs with the same longitudinal location but circumferentially offset relative to one another, and a second emitter that has a pair of electrode pairs with the same longitudinal location but circumferentially offset relative to one another, according to aspects of the present disclosure.

FIG. 14 provides an image of an exemplary shock wave catheter having a two emitters 1402 and 1406, each with longitudinally aligned electrode pairs 1404 and 1408, spaced along the length of the catheter. The longitudinally aligned electrode pairs 1404 and 1408 are circumferentially offset from one another but located at the same longitudinal location. In the example shown in FIG. 14, the electrode pairs 1404 of the first emitter 1402 are circumferentially aligned with the electrode pairs 1408 of the second emitter 1406.

Figure 15:
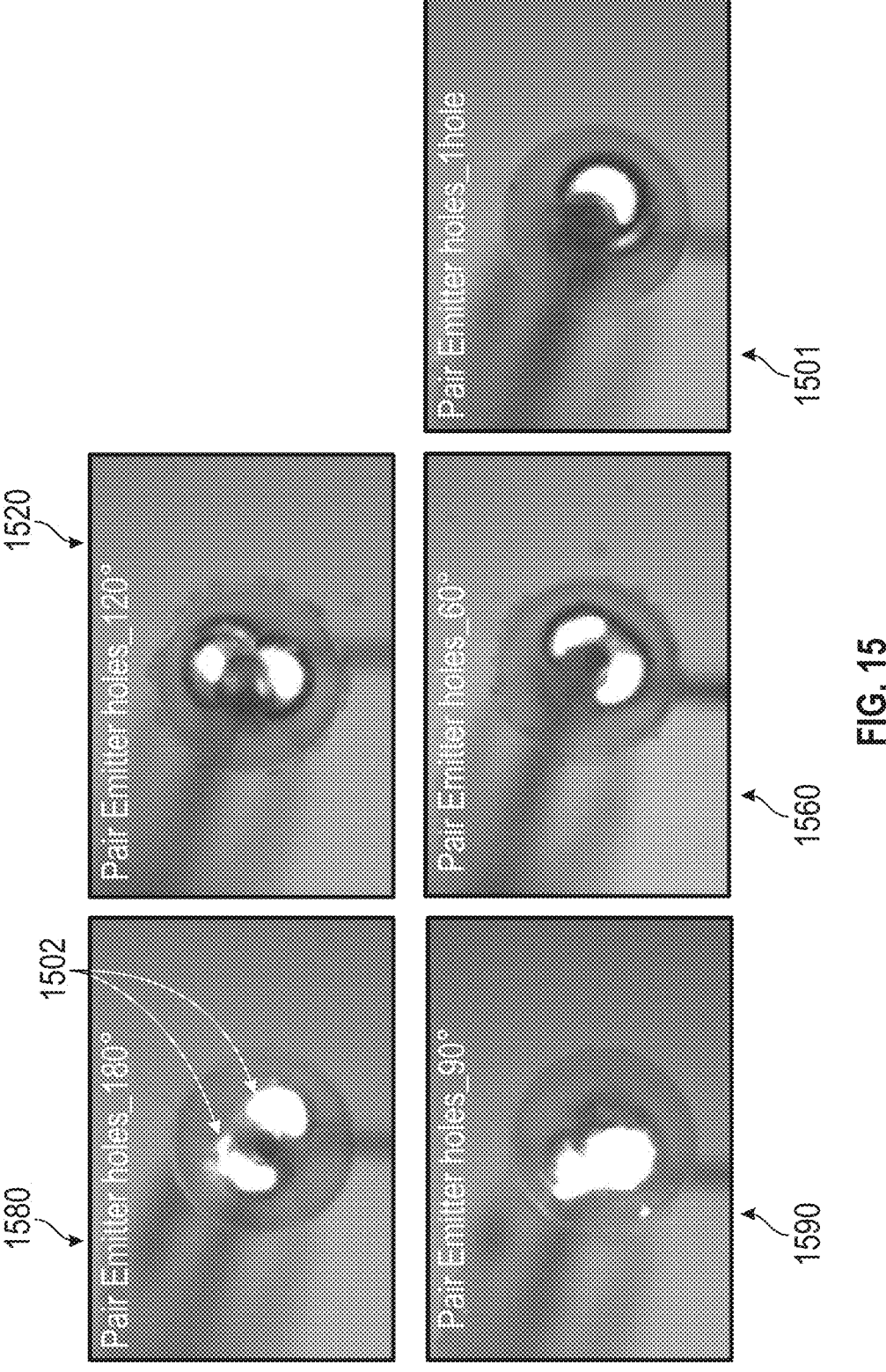
FIG. 15 provides a series of images of the formation and collapse of bubbles resulting from the activation of exemplary catheters, according to aspects of the present disclosure.

FIG. 15 provides a series of images of the formation and collapse of bubbles resulting from the activation of an exemplary shock wave catheter with an electrode assembly having a plurality of pairs of emitters with electrode pairs (referred to within the image as "emitter holes") that are longitudinally aligned but circumferentially offset from one another by 180 degrees, 120 degrees, 90 degrees, 60 degrees, and 0 degrees (i.e., where 0 degrees is an emitter with only one electrode pair), where the electrode pairs of emitter pair are circumferentially aligned with one another (e.g., the electrode pairs of a first sheath with a first pair of longitudinally aligned but circumferentially offset electrode pairs are circumferentially aligned with the electrode pairs of a second sheath with a second pair of longitudinally aligned but circumferentially offset electrode pairs) and closely located to one another (e.g., separated by a distance between 1 mm and 4 mm). More specifically, image 1580 corresponds to the offset of 180 degrees, image 1520 corresponds to the offset of 120 degrees, image 1590 corresponds to the offset of 90 degrees, image 1560 corresponds to the offset of 60 degrees, and image 1501 corresponds to an offset of 0 degrees.

As shown in image 1580, the bubbles 1502 generated by each electrode pair when offset by 180 degrees from one another do not interfere with one another. Accordingly, there is little to no constructive interference between shock waves generated by emitters offset by 180 degrees relative to one another. In comparison, as shown in images 1520, 1590, and 1560, the bubbles generated by each emitter when offset by 120 degrees, 90 degrees, and 60 degrees, respectively, from one another begin to merge together into one combined bubble. Thus, when offset by any of these degrees (e.g., 120 degrees, 90 degrees, 60 degrees), there is constructive interference between the bubbles generated by the emitters which tends to create a combined bubble.

Figure 16:
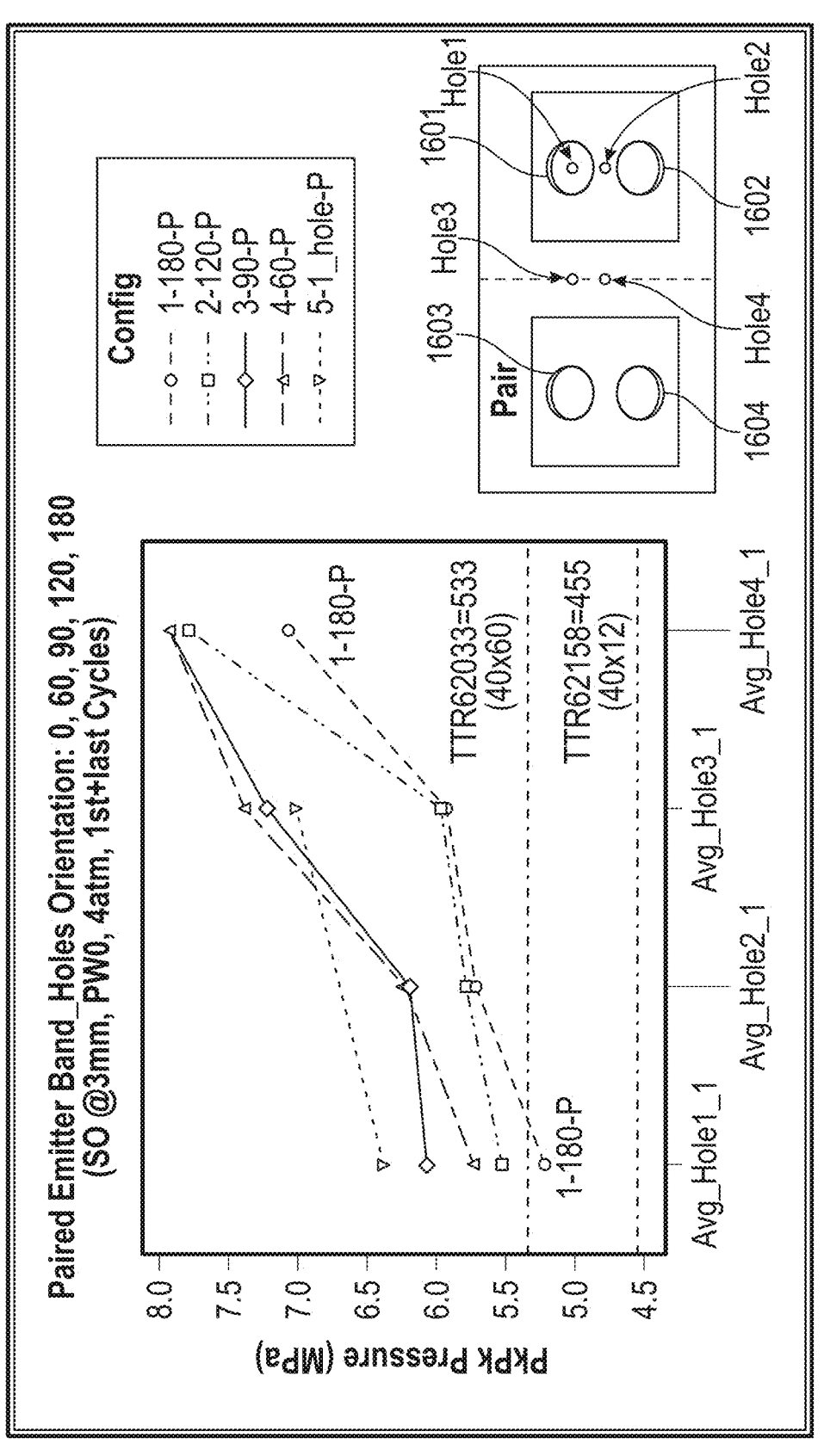
FIG. 16 provides a graph illustrating the pressure of acoustic wavefronts from a pair of emitters measured along the balloon edge of exemplary catheters, according to aspects of the present disclosure.

FIG. 16 provides a graph illustrating the pressure of acoustic wavefronts from a pair of emitters measured along the balloon edge of an exemplary catheter with an electrode assembly having a plurality of electrode pairs that are longitudinally aligned but circumferentially offset from one another by 180 degrees, 120 degrees, 90 degrees, 60 degrees, and 0 degrees, wherein the electrode pairs of each emitter pair are circumferentially aligned with one another. The pressure values shown in the graph of FIG. 16 are tabulated in Table 2 below.

is ~7 MPa, which is less than the peak pressure when the electrode pairs are offset by 120 degrees (~7.7 MPa), by 90 degrees (~7.9 MPa) and by 60 degrees (~7.9 MPa). Moreover, at every measurement location, the pressure values measured when the electrode pairs are offset by 120 degrees, 90 degrees, and 60 degrees, exceed the pressure values measured when the electrode pairs are offset by 180 degrees. Accordingly, electrode assemblies with pairs of emitters each having a pair of electrode pairs located at the same longitudinal location and offset by less than 180 degrees, such as the electrode assembly of FIGS. 13A-B, can realize greater pressure values than an electrode assembly with electrode pairs offset from one another by 180 degrees.

Figure 17:
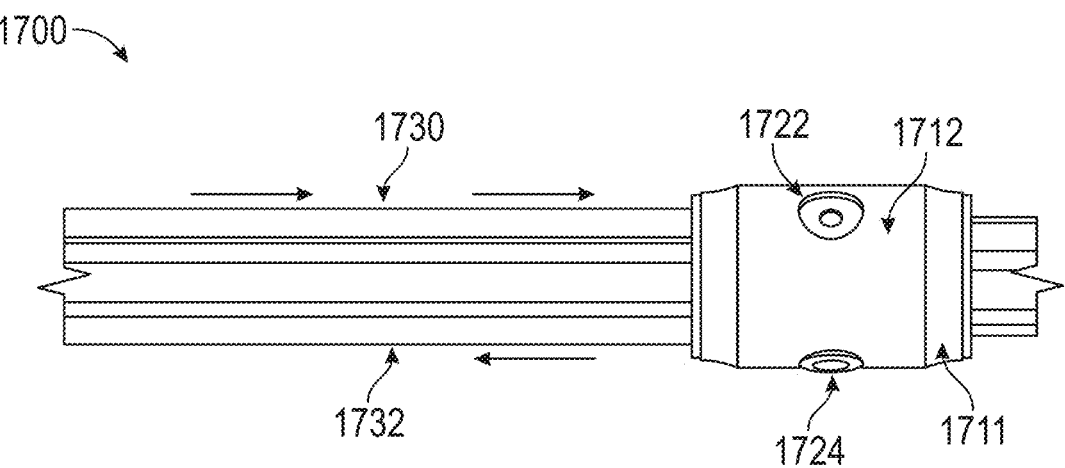
FIG. 17 illustrates an exemplary catheter electrode assembly having a emitter with a single electrode pair, according to aspects of the present disclosure.

FIG. 17 illustrates an exemplary catheter electrode assembly 1700 having a single emitter with a single electrode pair 1722. The electrode assembly 1700 is similar to the electrode assembly 900 of FIG. 9, except that here what would have been the second electrode pair is plugged via a plug 1724, meaning the electrode assembly 1700 includes a single hole electrode pair 1722 (e.g., a single cut-out in the sheath 1712). The electrode pair 1722 is formed from a conductive sheath 1712 and a number of wires 1730, 1732. As shown, the sheath 1712 includes a circular cut-out, however the electrode assembly 1700 can alternatively include an arcuate cut-out. When voltage is applied to the electrode assembly 1700, current flows between the cut-out of the conductive sheath 1712 (a first electrode) and an electrically conductive portion of an insulated wire (a second electrode) (e.g., an insulation removed portion of wire 1730) to generate shock waves. In one or more examples, the first insulated wire 1730 is located proximate to the cut-out of the sheath 1712 to form the electrode pair 1722, and the

TABLE 2

| Paired Emitters, Pressure values of a pair of two longitudinally aligned and circumferentially offset electrode pairs | | | | |
|---|---|---|---|---|
| | | Measurement Location | | |
| Offset Degree | Center of Electrode Pair 1 (1601) | Point between Electrode Pair 1 (1601) and Electrode Pair 2 (1602) | Centered between Electrode Pair 1 (1601) and Electrode Pair 3 (1603) | Centered location between Electrode Pair 1 (1601), Electrode Pair 2 (1602), Electrode Pair 3 (1603) and Electrode Pair 4 (1604) |
| 180 degrees | ~5.2 MPa | ~5.6 MPa | ~5.7 MPa | ~7 MPa |
| 120 degrees | ~5.5 MPa | ~5.65 MPa | ~5.75 MPa | ~7.7 MPa |
| 90 degrees | ~6 MPa | ~6.1 MPa | ~7.2 MPa | ~7.9 MPa |
| 60 degrees | ~5.7 MPa | ~6.15 MPa | ~7.4 MPa | ~7.9 MPa |
| 0 degrees | ~6.4 MPa | NA | ~7 MPa | NA |

As shown in the images of FIG. 15, when locating a pair of emitters at the same longitudinal location but circumferentially offset from one another by less than 180 degrees, the shock waves generated by the emitters tend to constructively interfere with one another to create a combined bubble. Furthermore, as shown in the graph of FIG. 16 and Table 2, locating a pair of longitudinally aligned and circumferentially offset electrode pairs such that they are closely longitudinally-adjacent to another pair of longitudinally aligned and circumferentially offset electrode pairs, wherein the circumferential offset is less than 180 degrees, tends to result with greater pressure values. For instance, when considering the centered location between every electrode pairs (e.g., electrode pairs 1601, 1602, 1603, and 1604), when the electrode pairs are offset by 180 degrees the peak pressure second insulated wire 1732 directly connected to the sheath 1712 (or alternatively connected via the plug 1724 when formed with a conductive material). When a high voltage pulse is applied across the first insulated wire 1730 and the second insulated wire 1732, a current may flow as indicated by the arrows, with the second insulated wire 1732 as a common ground wire (i.e., connecting to a group or negative channel of the high voltage pulse generator). In one or more examples, an insulation sheath 1711 can be positioned between the electrically conductive portions of the wire(s) and the cut-out(s) of the sheath 1712 to prevent unintended current flow between conductive portions of the wires and the conductive sheath, providing the path through which current can flow between the electrodes of the electrode pair 1722. In one or more examples, the electrode assembly 1700 can be considered to include a pair of electrode pairs that are circumferentially offset by 0 degrees.

Figure 18:
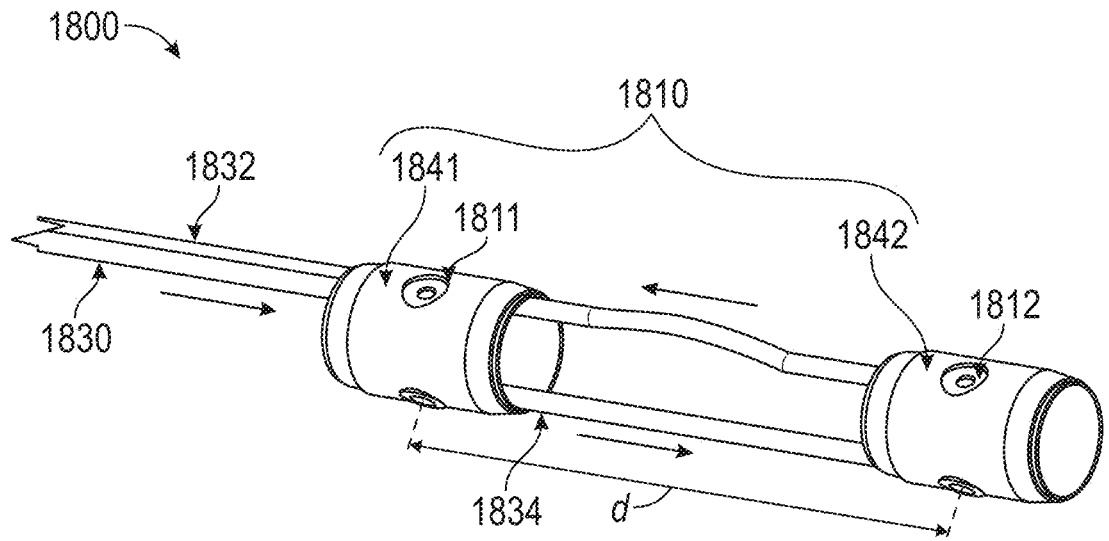
FIG. 18 illustrates a front right view of an exemplary electrode assembly having a pair of emitters, each with a single electrode pair, spaced apart along the length of the catheter, according to aspects of the present disclosure.

FIG. 18 illustrates a front right view of an exemplary electrode assembly 1800 having a pair of emitter electrode assemblies, each with a single electrode pair spaced apart along the length of the catheter. The electrode assembly 1800 includes a pair 1810 of closely spaced (e.g., longitudinally-adjacent) sheaths 1841, 1842, which each include a single electrode pair 1811 and 1812. The sheaths 1841 and 1842 of the electrode assembly 1800 are connected by a number of wires. As shown, each conductive sheath 1841, 1842 of the electrode assembly 1800 is located proximate to at least a portion of the insulated wires 1830, 1832, 1834. Each of the insulated wires 1830, 1832, 1834 includes an electrically conductive portion (not shown in figure) that is positioned near the cut-out electrode pairs 1811, 1812 on the conductive sheaths. For instance, a first insulated wire 1830 may extend along a tube (not shown) of the catheter and have an electrically conductive portion proximate to the circular cut-out (e.g., the hole) of sheath 1841, forming the first electrode pair 1811. A second insulated wire 1832 may extend to the sheath 1842 and have an electrically conductive portion proximate to the circular cut-out of the sheath 1842, forming the second electrode pair 1812. When a high voltage pulse is applied across the first insulated wire 1830 and the second insulated wire 1832, a current may flow as indicated by the arrows, with the second insulated wire 1832 as a common ground wire (i.e., connecting to a group or negative channel of the high voltage pulse generator).

As shown in FIG. 18, the electrode pair 1811 of sheath 1841 is circumferentially aligned with the electrode pair 1812 of sheath 1842 and separated from the electrode pair 1812 by a distance d. Accordingly, the electrode pairs 1811 and 1812 are longitudinally-adjacent and circumferentially aligned. As used to describe the electrode assembly 1800 of FIG. 18, d designates the distance between longitudinally-adjacent sheaths of an emitter pair. The distance d can also describe the distance between electrode pairs of those sheaths, for instance, the distance between electrode pair 1811 and electrode pair 1812, and/or distance between spark gaps of electrode pair 1811 and spark gaps of electrode pair 1812 (e.g., the gaps across which current jumps to generate a shock wave when voltage is applied to the electrodes of each electrode pair). In one or more examples, the distance between sheaths of an emitter pair can be between 1 mm and 4 mm, or at increments and gradients of distance within these values. In one or more examples, the distance d between sheaths 1841 and 1842 is 3.5 mm.

The shock waves emitted from the closely spaced (e.g., longitudinally-adjacent) and circumferentially aligned electrode pairs 1811 and 1812 of FIG. 18 can generate shock waves in a similar manner as the closely spaced and circumferentially aligned electrode pairs of the electrode assembly 400 of FIGS. 4A-C. Thus, in one or more examples, a sufficiently close distance d between the electrode pairs 1811 and 1812 can cause shock waves generated at each electrode pair to constructively interfere with each other to form one combined shock wave.

It should be noted that the elements and features of the example catheters illustrated in FIGS. 1, 2A-B, 3A-B, 4A-D, 5-12, 13A-B, and 14-18 may be rearranged, recombined, and modified without departing from the present invention. For instance, while FIGS. 2A-B, 3A-B, 4A-D, 9, 13A-B, 17, and 18 illustrate several example electrode assemblies, the present disclosure is intended to include catheters having a variety of electrode configurations, and the number, placement and spacing of the emitters and electrode pairs can modified without departing from the subject invention.

Further, while the emitters disclosed in examples herein have a construction typically having two electrode pairs on each emitter, it is contemplated to also include emitters having three electrode pairs (for example, circumferentially separated from each other by 120 degrees), four electrode pairs (for example, circumferentially separated from each other by 90 degrees), five electrode pairs (for example, circumferentially separated from each other by 72 degrees), six electrode pairs (for example, circumferentially separated from each other by 60 degrees), and so on. There may be physical limitations to the construction of such emitter assemblies relating to the size and arrangement of wiring, the ability to deliver sufficient power, the erosion profile of electrodes, and so on it is within the scope of the present disclosure that such emitters may be successfully developed with improvements in manufacturing capabilities.

Furthermore, numerical designators such as "first", "second", "third", "fourth", etc. are merely descriptive and do not indicate a relative order, location, or identity of elements or features described by the designators. For instance, a "first" shock wave may be immediately succeeded by a "third" shock wave, which is then succeeded by a "second" shock wave. As another example, a "third" emitter may be used to generate a "first" shock wave and vice versa. Accordingly, numerical designators of various elements and features are not intended to limit the disclosure and may be modified and interchanged without departing from the subject invention.

It will be understood that the foregoing is only illustrative of the principles of the invention, and that various modifications, alterations and combinations can be made by those skilled in the art without departing from the scope and spirit of the invention. Any of the variations of the various catheters disclosed herein can include features described by any other catheters or combination of catheters herein. Furthermore, any of the methods can be used with any of the catheters disclosed. Accordingly, it is not intended that the invention be limited, except as by the appended claims.

The invention claimed is:

1. A method for treating an occlusion in a body lumen, the method comprising:
   advancing a catheter comprising a guidewire lumen over a guidewire within a body lumen to a target treatment site; and
   generating shock waves using a first electrode pair at a first location of the catheter and a second electrode pair at a second location of the catheter such that the shock waves constructively interfere to produce a combined shock wave to treat an occlusion at the target treatment site.

2. The method of claim 1, wherein the first and second locations are longitudinally spaced apart in a longitudinal direction of the catheter.

3. The method of claim 2, wherein the first and second locations are spaced apart by 1 mm to 4 mm.

4. The method of claim 3, wherein the first and second locations are circumferentially aligned with respect to a longitudinal axis of the catheter.

5. The method of claim 1, wherein the first location is circumferentially offset from the second location with respect to a longitudinal axis of the catheter.

6. The method of claim 5, wherein the first and second locations are offset by an angle of less than 180 degrees.

7. The method of claim 5, wherein the first and second locations are longitudinally aligned with respect to the longitudinal axis of the catheter.

8. The method of claim 1, wherein a sheath forms an electrode of the first electrode pair.

9. The method of claim 1, wherein a first sheath forms an electrode of the first electrode pair and a second sheath forms an electrode of the second electrode pair.

10. The method of claim 9, wherein the first sheath forms an electrode of a third electrode pair that is at the same longitudinal location as the first electrode pair.

11. The method of claim 10, wherein the first electrode pair and the third electrode pair are circumferentially offset by an angle of 60 to 180 degrees.

12. The method of claim 9, wherein the second sheath forms an electrode of a fourth electrode pair.

13. The method of claim 1, comprising generating shock waves at third and fourth locations of the catheter such that the shock waves from the third and fourth locations constructively interfere to produce a combined shock wave that is different than the combined shock wave produced by the shock waves generated at the first and second locations.

14. The method of claim 13, wherein the shock waves generated at the third and fourth locations are generated independently of the shock waves generated at the first and second locations.

15. The method of claim 14, wherein the shock waves generated at the third and fourth locations do not constructively interfere with the shock waves generated at the first and second locations.

16. The method of claim 13, wherein the shock waves generated at the third and fourth locations are generated simultaneously with or up to a few nanoseconds apart from the shock waves generated at the first and second locations.

17. The method of claim 13, wherein the third and fourth locations are circumferentially offset from the first and second locations.

18. The method of claim 13, wherein the third and fourth locations are longitudinally spaced from the first and second locations in a longitudinal direction of the catheter.

19. The method of claim 1, wherein the combined shock wave propagates radially outwardly relative to a longitudinal axis of the catheter.

20. The method of claim 1, wherein the combined shock wave is produced within a flexible enclosure.

21. The method of claim 1, comprising filling a flexible enclosure enclosing the first and second locations prior to generating shock waves at the first and second locations of the catheter.

22. The method of claim 21, wherein the flexible enclosure is filled to a pressure of 2 atm to 4 atm.

23. A method for treating an occlusion in a body lumen, the method comprising:

advancing a catheter comprising a guidewire lumen over a guidewire within a body lumen to a target treatment site; and generating shock waves using a first laser light emitter at a first location of the catheter and a second laser light emitter at a second location of the catheter such that the shock waves constructively interfere to produce a combined shock wave to treat an occlusion at the target treatment site, wherein the first and second locations are longitudinally spaced apart in a longitudinal direction of the catheter.

24. The method of claim 23, wherein the first and second locations are spaced apart by 1 mm to 4 mm.

25. The method of claim 24, wherein the first and second locations are circumferentially aligned with respect to a longitudinal axis of the catheter.

26. The method of claim 23, wherein the first location is circumferentially offset from the second location with respect to a longitudinal axis of the catheter.

27. The method of claim 26, wherein the first and second locations are offset by an angle of less than 180 degrees.

28. The method of claim 26, wherein the first and second locations are longitudinally aligned with respect to the longitudinal axis of the catheter.

29. The method of claim 23, comprising generating shock waves using a third laser light emitter positioned at the same longitudinal location as the first laser light emitter.

30. The method of claim 29, wherein the first laser light emitter and the third laser light emitter are circumferentially offset by an angle of 60 to 180 degrees.

31. The method of claim 23, comprising generating shock waves at third and fourth locations of the catheter such that the shock waves from the third and fourth locations constructively interfere to produce a combined shock wave that is different than the combined shock wave produced by the shock waves generated at the first and second locations.

32. The method of claim 31, wherein the shock waves generated at the third and fourth locations are generated independently of the shock waves generated at the first and second locations.

33. The method of claim 32, wherein the shock waves generated at the third and fourth locations do not constructively interfere with the shock waves generated at the first and second locations.

34. The method of claim 31, wherein the shock waves generated at the third and fourth locations are generated simultaneously with or up to a few nanoseconds apart from the shock waves generated at the first and second locations.

35. The method of claim 31, wherein the third and fourth locations are circumferentially offset from the first and second locations.

36. The method of claim 31, wherein the third and fourth locations are longitudinally spaced from the first and second locations in a longitudinal direction of the catheter.

37. The method of claim 23, wherein the combined shock wave propagates radially outwardly relative to a longitudinal axis of the catheter.

38. The method of claim 23, wherein the combined shock wave is produced within a flexible enclosure.

39. The method of claim 23, comprising filling a flexible enclosure enclosing the first and second locations prior to generating shock waves at the first and second locations of the catheter.

40. The method of claim 39, wherein the flexible enclosure is filled to a pressure of 2 atm to 4 atm.

* * * * *